US012805716B2

(12) United States Patent
Inoue et al.

(10) Patent No.: US 12,805,716 B2
(45) Date of Patent: Nov. 24, 2026

(54) ENDOSCOPY IN REVERSIBLY ALTERED ANATOMY

(71) Applicant: Olympus Corporation, Tokyo (JP)

(72) Inventors: Shintaro Inoue, Westborough, MA (US); Anthony R. Pirozzi, Raleigh, NC (US)

(73) Assignee: Olympus Corporation, Tokyo (JP)

( * ) Notice: Subject to any disclaimer, the term of this patent is extended or adjusted under 35 U.S.C. 154(b) by 244 days.

(21) Appl. No.: 18/540,074

(22) Filed: Dec. 14, 2023

(65) Prior Publication Data

US 2024/0197163 A1 Jun. 20, 2024

Related U.S. Application Data

(60) Provisional application No. 63/387,838, filed on Dec. 16, 2022, provisional application No. 63/387,537, filed on Dec. 15, 2022.

(51) Int. Cl.

*A61B 1/273* (2006.01)
*A61B 1/00* (2006.01)
*A61B 1/045* (2006.01)
*A61B 17/00* (2006.01)

(52) U.S. Cl.

CPC ........ *A61B 1/2736* (2013.01); *A61B 1/00039* (2013.01); *A61B 1/00135* (2013.01); *A61B 1/045* (2013.01); *A61B 17/0057* (2013.01)

(58) Field of Classification Search

CPC ............ A61B 1/00039; A61B 1/00135; A61B 1/045; A61B 1/2736; A61B 17/0057; A61B 2017/00278

See application file for complete search history.

(56) References Cited

U.S. PATENT DOCUMENTS

2004/0138760 A1* 7/2004 Schurr .................. A61F 5/0083 623/23.65
2005/0256587 A1* 11/2005 Egan ......................... A61F 2/04 604/9
2007/0213687 A1* 9/2007 Barlow ............. A61M 25/0662 604/523
2022/0362045 A1* 11/2022 Cairo Nunes ........... A61F 5/003
2023/0148849 A1* 5/2023 Inoue ................. A61B 1/00133 600/101

* cited by examiner

*Primary Examiner* — Aaron B Fairchild

(74) *Attorney, Agent, or Firm* — Schwegman Lundberg & Woessner, P.A.

(57) ABSTRACT

Systems, devices, and methods for endoluminal transgastric access to the pancreaticobiliary anatomy are disclosed. An exemplary transgastric access technique comprises creating a reversible alteration of gastric anatomy using a closing device, including a reversible disconnection between a first gastric portion and a second gastric portion via an alterable gastric closure. The technique further includes, during an endoscopy procedure, passing a steerable elongate instrument into the first gastric portion, identifying the alterable gastric closure, and disengaging at least a portion of the alterable gastric closure using an endoluminal disengaging device to at least partially reconnect the first and second gastric portions. The steerable elongate instrument can then pass through the disengaged portion and extend into the pancreaticobiliary anatomy to perform the endoscopic procedure therein. The disengaged portion can be closed using the alterable gastric closure at the conclusion of the procedure.

15 Claims, 22 Drawing Sheets

ENDOSCOPY IN REVERSIBLY ALTERED ANATOMY

CROSS-REFERENCE TO RELATED APPLICATIONS

This application is based upon and claims the benefit of priority to U.S. Provisional Application Ser. No. 63/387,537, filed on Dec. 15, 2022, and U.S. Provisional Application Ser. No. 63/387,838, filed on Dec. 16, 2022, the entire contents of which is incorporated herein by reference.

FIELD OF THE DISCLOSURE

The present document relates generally to endoscopy systems, and more particularly to systems and methods for endoscopically accessing patient pancreaticobiliary system via a reversibly altered gastric anatomy.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region may include gastrointestinal (GI) tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct Per-Oral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

Diagnostic or therapeutic endoscopy such as ERCP and DPOC is generally performed via an endoluminal route in the upper GI tract. Some patients may have surgical alterations of a portion of GI tract (e.g., stomach) or the pancreaticobiliary system. Surgically altered anatomy can be a clinical challenge for pancreaticobiliary endoscopy.

SUMMARY

The present disclosure recognizes several technological problems to be solved with conventional endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

Another challenge in conventional endoscopy is a high degree of variability of patient anatomy, especially in patients with surgically altered anatomy. For example, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. Some patients have altered papilla anatomy or otherwise difficult to access. With the duodenoscope designed to be stable in the duodenum, it can be more difficult to reach the duodenal papilla in surgically altered anatomy. Conventional endoscopy systems generally lack the capability of providing cannulation and endoscope navigation guidance based on patient's unique anatomy.

Anatomical surgical alterations of the upper gastrointestinal (GI) tract have been a clinical challenge for performing diagnostic and therapeutic endoscopy, especially when pancreaticobiliary diseases are involved. Esophagectomy, gastrectomy with various reconstructions and pancreaticoduodenectomy are among the most common surgeries causing upper GI tract alterations. GI post-surgical alteration anatomy may also represent for endoscopic ultrasound (EUS) a hurdle for pancreatic examination and tissue acquisition such as due to the difficulty in achieving adequate scans of the pancreas or the distal bile duct, while on the other, it could be insurmountable to achieve the papillary region or the bilioenteric anastomosis during standard ERCP.

Proper knowledge of the anatomical alterations has been fundamental to perform endoscopy in such patients. For example, Roux-en-Y-Gastric Bypass (RYGB) surgery is one of the most common bariatric surgeries for obesity patients. The RYGB is a gastric bypass procedure performed laparoscopically by the surgeon to divide the stomach into a smaller upper portion (gastric pouch) and a lower majority of the stomach using surgical titanium staples, where the gastric pouch is then surgically attached to a middle portion of the small intestine (e.g., jejunum), thereby bypassing the rest of the stomach and the duodenum (upper portion of the small intestine). The gastric pouch restricts the amount of food intake and absorption of fewer calories and nutrients from the food. Pancreaticobiliary endoscopy, such as ERCP, in post-RYGB patients depends on the knowledge of the anatomic alteration and physician operator's experience. Moreover, even experienced physicians may not be able to find the way to obtain adequate window, and to move an endoscope through an altered anatomy, especially when anastomotic reconstructions are unclear or particularly laborious.

An existing approach for performing ERCP in altered anatomy such as post-RYGB patients is EUS-directed transgastric ERCP (EDGE). This technique involves creation of a fistulous tract by placing a lumen-apposing metal stent (LAMS) under EUS guidance between either the jejunum or gastric pouch to the excluded lower stomach portion, and subsequently performing conventional ERCP through the LAMS. However, placing the stent between two separated lumens under the EUS guidance can be technically and practically challenging. This is at least because the RYGB procedure is irreversible and designed to be permanent (the surgical titanium staples used for creating the gastric pouch will stay in the body forever), and the inadequate EUS scans and limited structure information obtainable from the EUS images. Additionally, EDGE procedure may also cause adverse events such as LAMS maldeployment and migration.

The present disclosure can help solve these and other problems by providing systems, devices, and methods for improved pancreaticobiliary endoscopy in a reversibly altered gastric anatomy. According to one aspect of the present disclosure, a pancreaticobiliary endoscopy technique comprises creating a reversible alteration of gastric anatomy using a closing device, including reversibly disconnecting a first gastric portion from a second gastric portion using an alterable gastric closure. The reversible disconnection can be created using an endoluminal approach (e.g., via an endoluminal closing device associated with an endoluminal instrument such as an endoscope), or alternatively using a laparoscopic approach. The technique further includes, during pancreaticobiliary endoscopy procedure (e.g., ERCP), passing an endoscope down to the first gastric portion, identifying the alterable gastric closure that reversibly disconnects the first and second gastric portions, and disengaging at least a portion of the alterable gastric closure using an endoluminal disengaging device operably disposed at a distal portion of the endoscope. The disengagement establishes at least a partial reconnection between the first and second gastric portions. The endoscope can then be extended through the disengaged portion of the alterable gastric closure into the second gastric portion, and further into the pancreaticobiliary anatomy to perform diagnostic or therapeutic operation therein. At the conclusion of the endoscopic procedure, the disengaged portion can be reclosed using the alterable gastric closure, thereby reversibly dividing the first and the second gastric portions.

The pancreaticobiliary endoscopy technique described in this disclosure provides an improved transgastric approach for accessing the pancreaticobiliary anatomy in patients with altered anatomy of upper GI tract. In contrast to conventional RYGB which produces an irreversible and permanent gastric division, the apparatus and techniques described herein can be used to create reversible division of gastric anatomy that allows for and facilitates standard transgastric approach of pancreaticobiliary endoscopy. Procedures such that conventional anterograde ERCP can be performed using endoscopes through stomach and duodenum to the papilla. Compared to conventional techniques such as EDGE in RYGB anatomy, the reversable gastric division described herein avoids percutaneous staple removal and stent placement, is easier to operate, and reduces the chances of complications and adverse events associated with EDGE. As a result, the overall procedure success rate can be improved, and the healthcare cost associated with complications and procedure failures can be reduced.

Example 1 is a method for endoluminal transgastric access to a pancreaticobiliary anatomy of a patient, the method comprising: creating a reversible alteration of gastric anatomy in the patient, including reversibly disconnecting a first gastric portion from a second gastric portion using an alterable gastric closure and a closing device; during an pancreaticobiliary endoscopy procedure: passing a steerable elongate instrument through a portion of gastrointestinal (GI) tract into the first gastric portion; identifying the alterable gastric closure that reversibly disconnects the first and second gastric portions; disengaging at least a portion of the alterable gastric closure using an endoluminal disengaging device operably disposed at a distal portion of the steerable elongate instrument, the disengagement at least partially reconnecting the first and second gastric portions; and extending the steerable elongate instrument through the disengaged portion of the alterable gastric closure into the second gastric portion and further into the pancreaticobiliary anatomy to perform diagnostic or therapeutic operation therein.

In Example 2, the subject matter of Example 1 optionally includes, further comprising, at a conclusion of the pancreaticobiliary endoscopy procedure, reapplying an alterable gastric closure to reversibly disconnect the first gastric portion from the second gastric portion using the closing device.

In Example 3, the subject matter of any one or more of Examples 1-2 optionally include, wherein the diagnostic or therapeutic operation includes an endoscopic cholangiopancreatography (ERCP) procedure or a direct peroral cholangioscopy (DPOC) procedure.

In Example 4, the subject matter of any one or more of Examples 1-3 optionally include, wherein the first and second gastric portions are respectively a gastric pouch and an excluded stomach portion identified in a gastric bypass procedure.

In Example 5, the subject matter of any one or more of Examples 1-4 optionally include, wherein reversibly disconnecting the first gastric portion from the second gastric portion includes using an endoluminal closing device operably disposed at a distal portion of the steerable elongate instrument.

In Example 6, the subject matter of any one or more of Examples 1-5 optionally include, wherein the alterable gastric closure includes at least one of: alterable sutures; alterable glue; or alterable clips.

In Example 7, the subject matter of any one or more of Examples 1-6 optionally include: identifying position and posture of one or more of the closing device or the endoluminal disengaging device; and providing the identified position and posture of one or more of the closing device or the endoluminal disengaging device to a user on a user interface, or to a robotic endoscopy system to facilitate robotic manipulation of the closing device or the endoluminal disengaging device.

In Example 8, the subject matter of Example 7 optionally includes receiving endoscopic image of the portion of the GI tract, wherein identifying the position and posture of one or more of the closing device or the endoluminal disengaging device is based at least on the received endoscopic image.

In Example 9, the subject matter of any one or more of Examples 7-8 optionally include detecting electromagnetic (EM) wave emitted from an EM emitter associated with one or more of the closing device or the endoluminal disengaging device, wherein identifying the position and posture of one or more of the closing device or the endoluminal disengaging device is based at least on the detected EM waves.

In Example 10, the subject matter of any one or more of Examples 8-9 optionally include: receiving from the user interface a user input identifying closing site and trajectory on the endoscopic image of the portion of the GI tract; and robotically manipulating the closing device to apply the alterable gastric closure to the identified closing site and trajectory.

In Example 11, the subject matter of any one or more of Examples 8-10 optionally include, when creating the reversible alteration of gastric anatomy: identifying position and posture of a laparoscopic device used in a gastric bypass procedure from the endoscopic image; and presenting the endoscopic image of the portion of the GI tract and the identified position and posture of the laparoscopic device to a user on a user interface.

In Example 12, the subject matter of any one or more of Examples 7-11 optionally include: receiving an endoscopic image of the portion of the GI tract during the pancreaticobiliary endoscopy procedure; identifying disengaging site and trajectory in proximity to the alterable gastric closure from the received endoscopic image; and robotically manipulating the endoluminal disengaging device to disengage at least the portion of the alterable gastric closure from the identified disengaging site and trajectory.

In Example 13, the subject matter of Example 12 optionally includes receiving a user input identifying the disengagement site and trajectory from the endoscopic image.

In Example 14, the subject matter of any one or more of Examples 12-13 optionally include, wherein identifying the disengaging site and trajectory includes detecting a marker on at least a portion of the alterable gastric closure being applied when creating the reversible alteration of gastric anatomy.

In Example 15, the subject matter of any one or more of Examples 1-14 optionally include presenting on a user interface an interactive and navigable view of an image of the reversibly altered gastric anatomy with distinct landmarks.

Example 16 is an endoscopic system comprising: a steerable elongate instrument configured for transgastric access to a pancreaticobiliary anatomy of a patient through a portion of gastrointestinal (GI) tract; a closing device configured to reversibly alter gastric anatomy including reversibly disconnecting a first gastric portion from a second gastric portion using an alterable gastric closure; and an endoluminal disengaging device operably disposed at a distal portion of the steerable elongate instrument, the endoluminal disengaging device configured to disengage at least a portion of the alterable gastric closure during a pancreaticobiliary endoscopy procedure and thereby at least partially reconnecting the first and second gastric portions to facilitate transgastric access to a pancreaticobiliary anatomy via the steerable elongate instrument.

In Example 17, the subject matter of Example 16 optionally includes, wherein the closing device includes an endoluminal closing device operably disposed at a distal portion of the steerable elongate instrument.

In Example 18, the subject matter of any one or more of Examples 16-17 optionally include, wherein the alterable gastric closure includes at least one of: alterable sutures; alterable glue; or alterable clips.

In Example 19, the subject matter of any one or more of Examples 16-18 optionally include a controller circuit configured to: identify position and posture of one or more of the closing device or the endoluminal disengaging device; and provide the identified position and posture of one or more of the closing device or the endoluminal disengaging device to a user on a user interface, or to a robotic endoscopy system to facilitate robotic manipulation of closing device or the endoluminal disengaging device.

In Example 20, the subject matter of Example 19 optionally includes, wherein the steerable elongate instrument includes an endoscope configured to produce an endoscopic image of the portion of the GI tract, wherein the controller circuit is configured to identify the position and posture of one or more of the closing device or the endoluminal disengaging device based at least on the endoscopic image.

In Example 21, the subject matter of any one or more of Examples 19-20 optionally include: an electromagnetic (EM) wave emitter associated with the closing device or the endoluminal disengaging device, the EM wave emitter configured to emit EM waves; and an external EM wave detector configured to detect the emitted EM waves, wherein the controller circuit is configured to identify the position and posture of one or more of the closing device or the endoluminal disengaging device based at least on the detected EM waves.

In Example 22, the subject matter of any one or more of Examples 20-21 optionally include, wherein the controller circuit is configured to: receive from the user interface a user input identifying closing site and trajectory on the image of the portion of the GI tract; and generate a control signal to an actuator of a robotic system to robotically manipulate the closing device to apply the alterable gastric closure to the identified closing site and trajectory.

In Example 23, the subject matter of any one or more of Examples 19-22 optionally include, wherein the controller circuit is configured to: receive an endoscopic image of the portion of the GI tract during the pancreaticobiliary endoscopy procedure; identify disengaging site and trajectory in proximity to the alterable gastric closure from the received endoscopic image; and generate a control signal to an actuator of a robotic system to robotically manipulate the endoluminal disengaging device to disengage at least the portion of the alterable gastric closure from the identified disengaging site and trajectory.

In Example 24, the subject matter of Example 23 optionally includes, wherein to identify the disengaging site and trajectory, the controller circuit is configured to receive from the user interface a user input identifying the disengagement site and trajectory from the endoscopic image.

In Example 25, the subject matter of any one or more of Examples 23-24 optionally include, wherein to identify the disengaging site and trajectory, the controller circuit is configured to automatically detect a marker on at least a portion of the alterable gastric closure being applied when creating the reversible alteration of gastric anatomy.

In Example 26, the subject matter of any one or more of Examples 19-25 optionally include a user interface configured to present an interactive and navigable view of an image of the reversibly altered gastric anatomy with distinct landmarks.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

This document describes systems, devices, and methods for providing endoluminal transgastric access to pancreaticobiliary anatomy in an endoscopic procedure. According to an example, a pancreaticobiliary endoscopy technique comprises creating a reversible alteration of gastric anatomy using a closing device, including a reversible disconnection between a first gastric portion and a second gastric portion via an alterable gastric closure. The reversible disconnection can be created using an endoluminal approach, or alternatively a laparoscopic approach. The technique further includes, in an pancreaticobiliary endoscopy procedure, passing an endoscope through the GI tract into the first gastric portion, identifying the alterable gastric closure, and disengaging at least a portion of the alterable gastric closure using an endoluminal disengaging device. The disengagement establishes at least partial reconnection between the first and second gastric portions. The endoscope is then extended through the disengaged portion of the alterable gastric closure into the second gastric portion and further into the pancreaticobiliary anatomy to perform diagnostic or therapeutic operation therein. At the conclusion of the endoscopic procedure, the disengaged portion can be closed using the alterable gastric closure.

Figure 1:
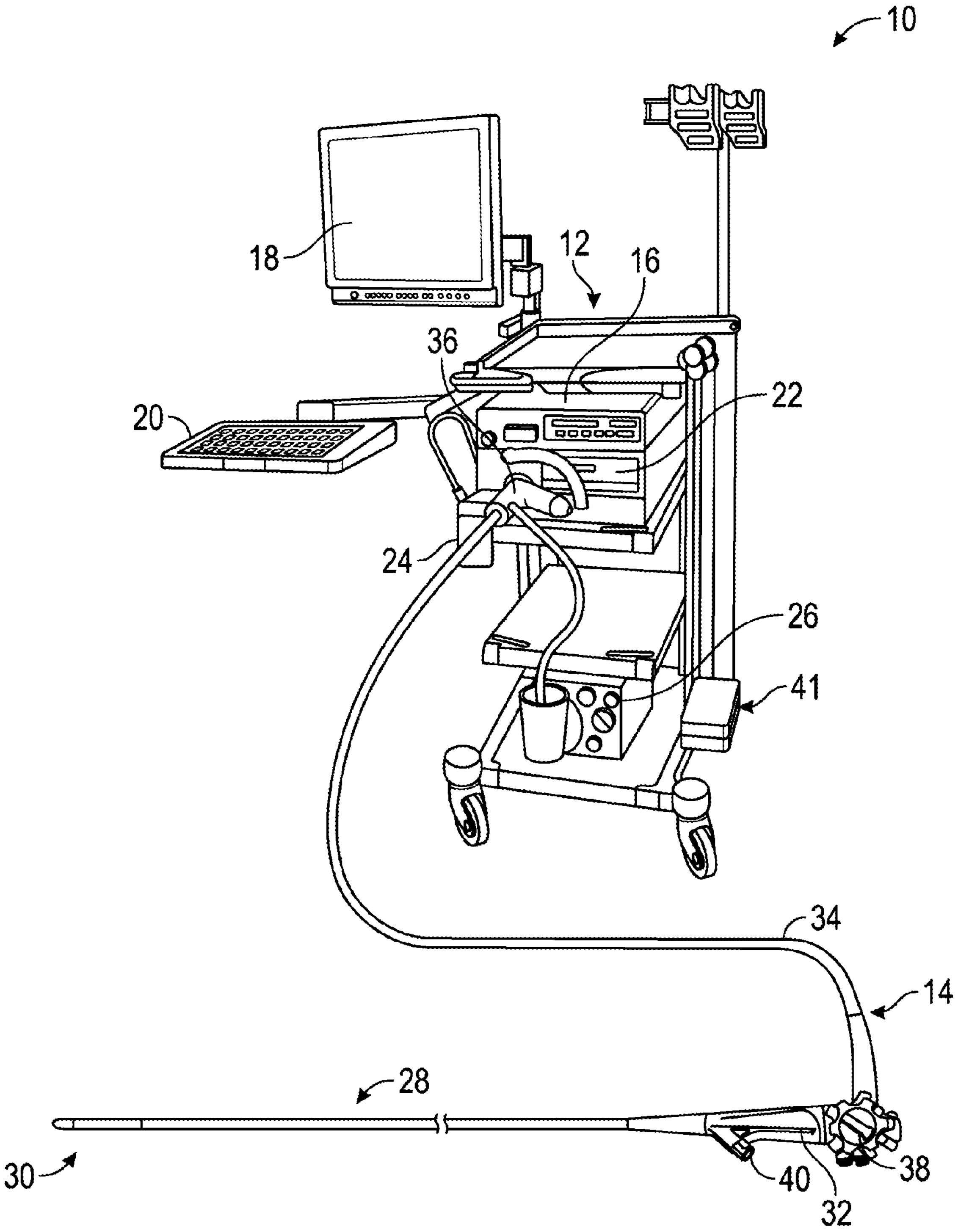
FIGS. 1-2 are schematic diagrams illustrating an example of an endoscopy system for use in endoscopic procedures such as an ERCP procedure.

FIG. 1 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 may include various ports for coupling with endoscopy system 10. For example, the control unit 16 may include a data input/output port for receiving data from and communicating data to the endoscope 14. The light source 22 may include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by an operator of endoscopy system 10 to control functions of endoscopy system 10 and view output of endoscope 14. In some examples, the control unit 16 can additionally be used to generate signals or other outputs for treating the anatomical region into which the endoscope 14 is inserted. Examples of such signals or outputs may include electrical output, acoustic output, a radio-frequency energy output, a fluid output and the like for treating the anatomical region with, for example, cauterizing, cutting, freezing and the like.

The endoscope 14 can interface with and connect to the imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope. The working channel can extend between handle section 32 and functional section 30. Additional functionalities, such as fluid passages, guidewires, and pull wires can also be provided by insertion section 28 (e.g., via suction or irrigation passageways, and the like).

The handle section 32 can comprise a control knob 38 and ports 40. The ports 40 can be configured to couple various electrical cables, guidewires, auxiliary scopes, tissue collection devices of the present disclosure, fluid tubes and the like to handle section 32 for coupling with insertion section 28. The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 2) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 2), etc. Alternatively, several components of the imaging and control system 12 shown in FIGS. 1 and 2 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

Figure 2:
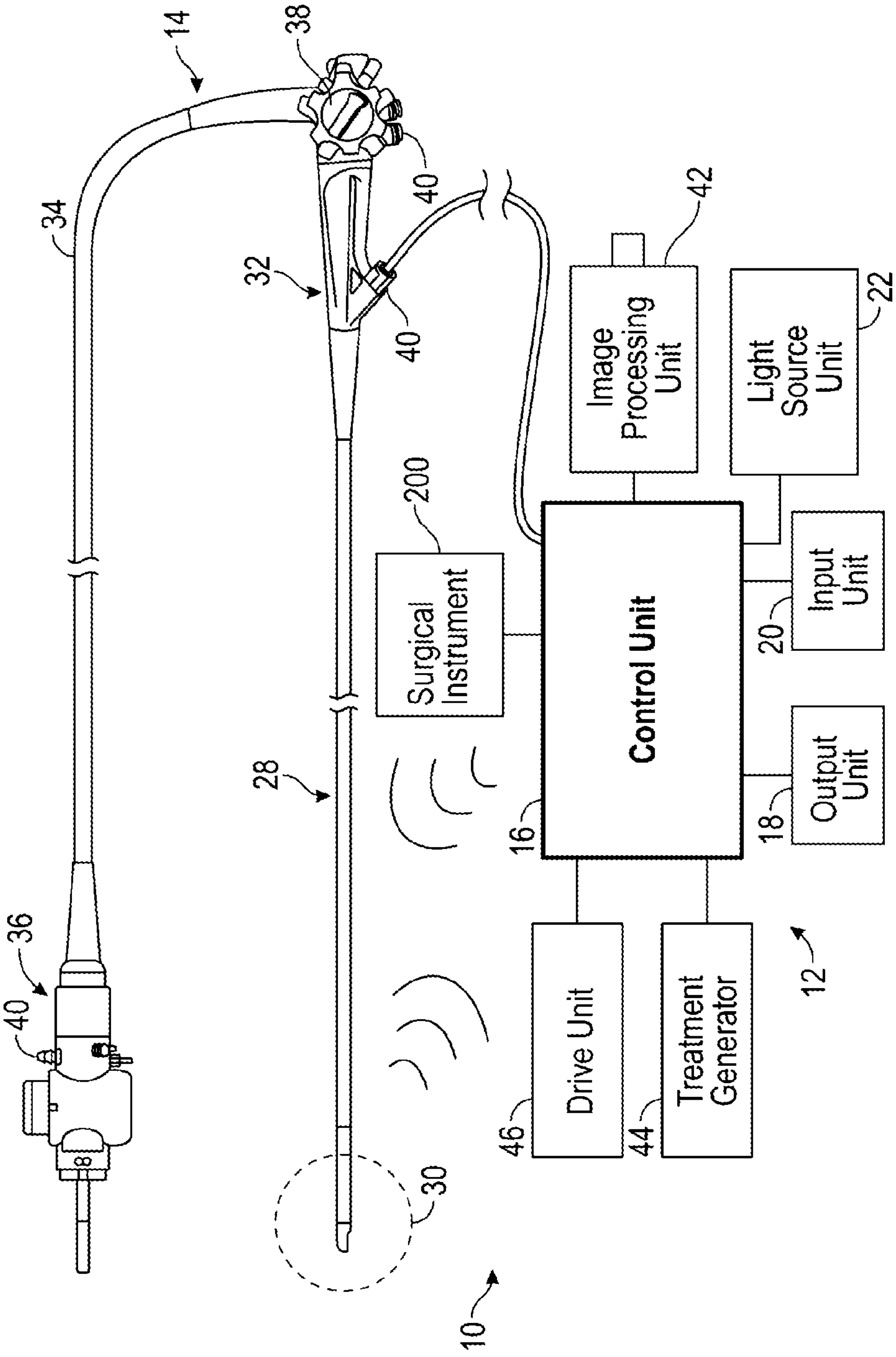

FIG. 2 is a schematic diagram of the endoscopy system 10 shown in FIG. 1, which comprises the imaging and control system 12 and the endoscope 14. FIG. 2 schematically illustrates components of the imaging and control system 12 coupled to the endoscope 14, which in the illustrated example comprises a duodenoscope. The imaging and control system 12 can comprise a control unit 16, which may include or be coupled to an image processing unit 42, a treatment generator 44, and a drive unit 46, as well as the light source 22, the input unit 20, and the output unit 18 as discussed above with reference to FIG. 1. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which may include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 may include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

The treatment generator 44 can generate a treatment plan, which can be used by the control unit 16 to control the operation of the endoscope 14, or to provide with the operating physician a guidance for maneuvering the endoscope 14, during an endoscopic procedure. In an example, the treatment generator 44 can generate an endoscope navigation plan, including estimated values for one or more cannulation or navigation parameters (e.g., an angle, a force, etc.) for maneuvering the steerable elongate instrument, using patient information including an image of the target anatomy. The endoscope navigation plan can help guide the operating physician to cannulate and navigate the endoscope in the patient anatomy. The endoscope navigation plan may additionally or alternatively be used to robotically adjust the position, angle, force, and/or navigation of the endoscope or other instrument. Examples of endoscope navigation plan are discussed below with reference to FIGS. 5A-5B.

Figure 3A:
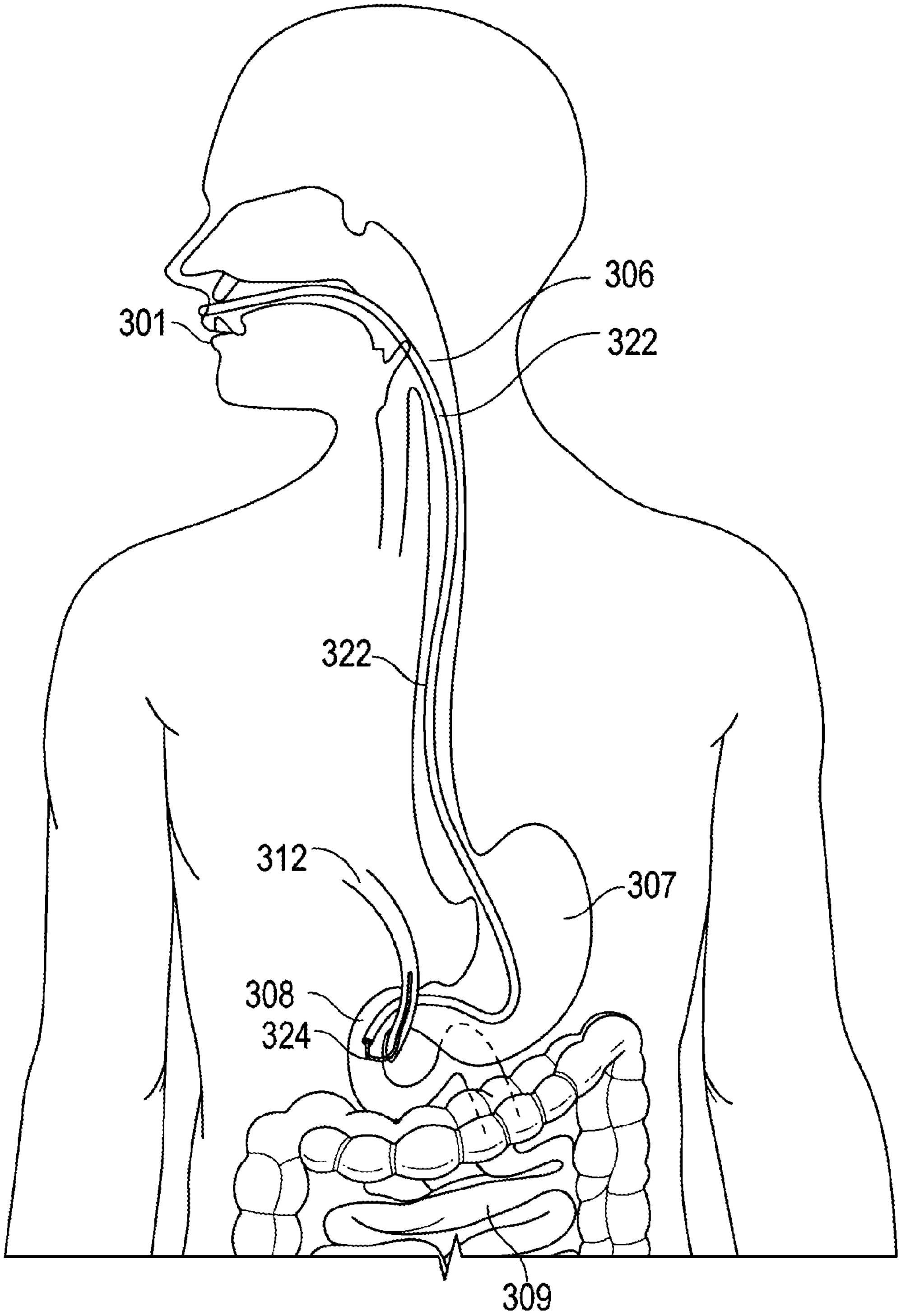
FIG. 3A-3B illustrates an example of peroral cholangioscopy performed using a cholangioscope into the bile duct and a portion of patient anatomy where the procedure is performed.
Figure 3B:
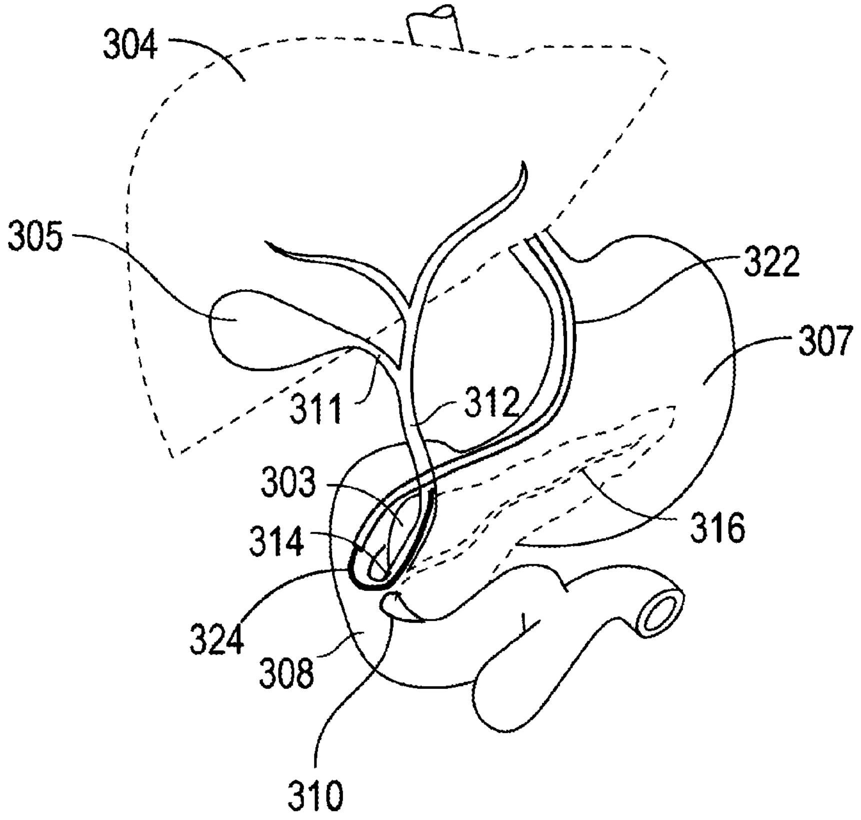

FIG. 3 is a diagram illustrating an example of peroral cholangioscopy (e.g., ERCP or DPOC) performed using a cholangioscope 324 into the bile duct and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310. The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

Figure 4:
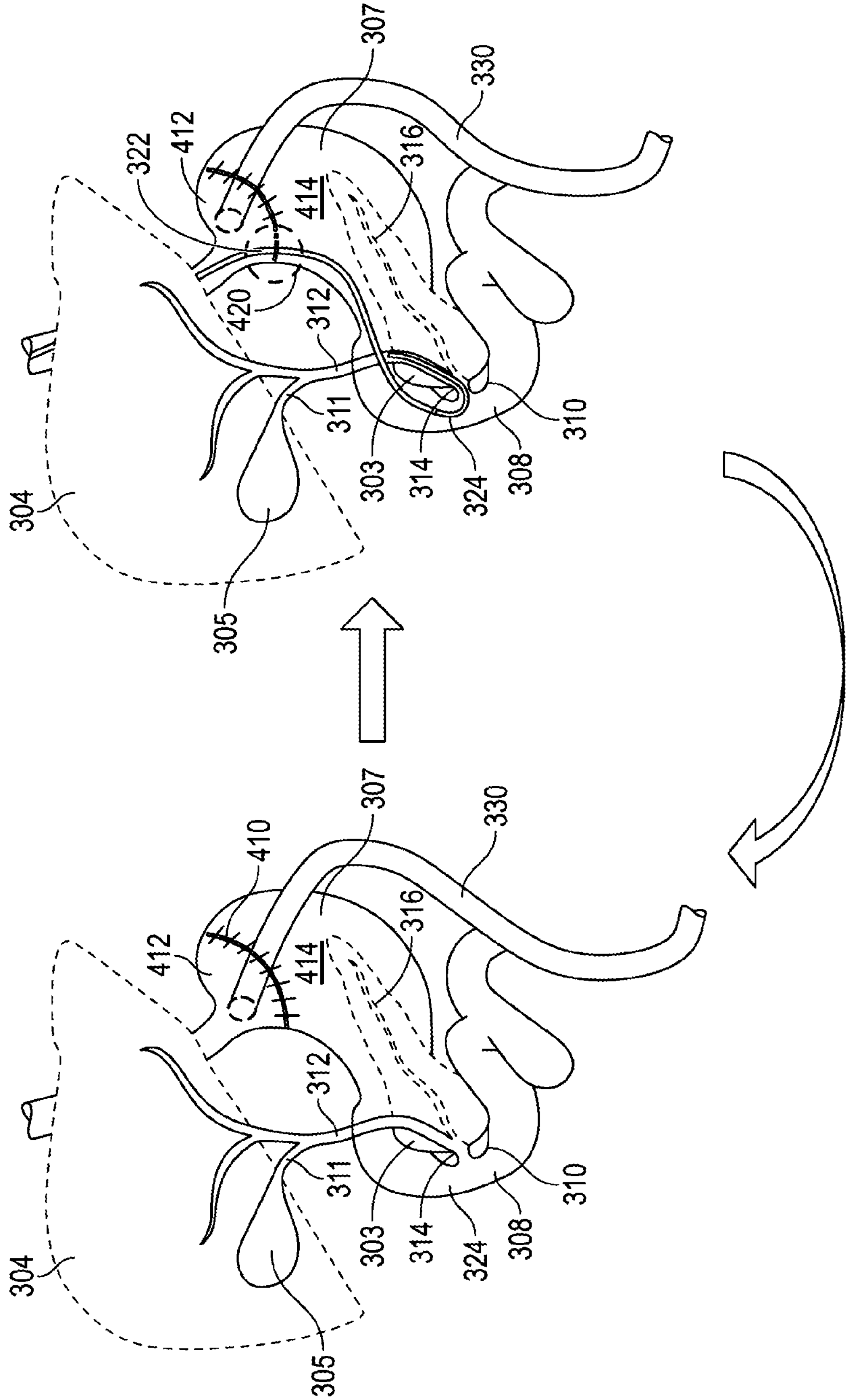
FIG. 4 illustrates an example of peroral cholangioscopy where an endoscope is fed through a reversibly altered gastric anatomy and into the pancreaticobiliary system.

FIG. 4 is a diagram illustrating an example of peroral cholangioscopy (e.g., ERCP or DPOC) where an endoscope is fed through a reversibly altered gastric anatomy and into the pancreaticobiliary system. The pancreaticobiliary system includes common bile duct 312 connected to the duodenum 308 via duodenal papilla 314. Common bile duct 312 can branch off into pancreatic duct 316 and gallbladder duct 311. Duodenal papilla 314 may include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it is common during medical procedures to cut sphincter of Oddi 310 to enlarge duodenal papilla 314 to allow for easier access of instrument into common bile duct 312.

FIG. 4 illustrates an example of reversibly altered gastric anatomy, where an alterable gastric closure 410 reversibly divides the stomach 307 into a first gastric portion 412 and a second gastric portion 414. Such division of the stomach is similar to the gastric division in conventional RYGB procedure for bariatric (weight loss) treatment, where the stomach is divided into an upper gastric pouch and a lower majority of the stomach, where the gastric pouch is surgically attached to a middle portion of the small intestine 330 such as a portion of the jejunum. However, unlike the irreversible and permanent gastric division in RYGB procedure, the alterable gastric closure 410 is a reversible and non-permanent closure; and as to be described below with reference to FIG. 4, the alterable gastric closure 410 can be at least partially disengaged to establish at least partial reconnection between the first gastric portion 412 and the second gastric portion 414. Examples of the alterable gastric closure 410 may include sutures, glue, or clips, among other alterable closing means. The alterable gastric closure 410 can be created using a closing device prior to an pancreaticobiliary endoscopic procedure. The closing device can be associated with a surgical device, such as an endoscope (or other endoluminal instrument), or a laparoscope. In an example, the closing device is an endoluminal closing device operably disposed at a distal portion of the endoscope, such as the cholangioscope 324. In an example, the endoluminal closing device can be at least partially robotically controlled via an actuator, as described further below with reference to FIG. 5A.

FIG. 4 illustrates an example of partial disengagement of the alterable gastric closure 410 previously created during the pancreaticobiliary endoscopic procedure. The disengagement can be made using a disengaging device. The disengaging device can be associated with a surgical device, such as an endoscope (or other endoluminal instrument), or a laparoscope. In an example, the disengaging device is an endoluminal disengaging device operably disposed at a distal portion of the endoscope, such as the cholangioscope 324. In an example, the disengaging device may include endoscopic scissors operable to cut the alterable gastric closure 410 (e.g., sutures). In an example, the disengaging device can be robotically controlled via an actuator, as described further below with reference to FIG. 5B. The disengaged portion 420 of the alterable gastric closure 410 can form an opening that at least partially reconnects the first gastric portion 412 and the second gastric portion 414. The opening can be sized and shaped to allow the endoscope or the sheath 322 to pass therethrough. The endoscope or the sheath 322 can pass the second gastric portion 414 and the duodenum 308, and reach the duodenal papilla 314. The cholangioscope 324 can extend from guide sheath 322, and extend into common bile duct 312 to perform intended diagnostic or therapeutic procedures therein.

At the conclusion of the endoscopic procedure, the endoscope can be retracted, and the disengaged portion 420 can be re-closed using the alterable gastric closure 410 as depicted in FIG. 4. The second gastric portion 414 remains to be bypassed by the small intestine 330 being connected to the first gastric portion 412, and the bariatric (weight loss) treatment would not be affected. If and when the patient needs another pancreaticobiliary endoscopy procedure, another disengaging procedure can be performed to create a disengagement portion similar to the disengaged portion 420 to allow the endoscope to pass therethrough and achieve transgastric access to the pancreaticobiliary system.

Figure 5A:
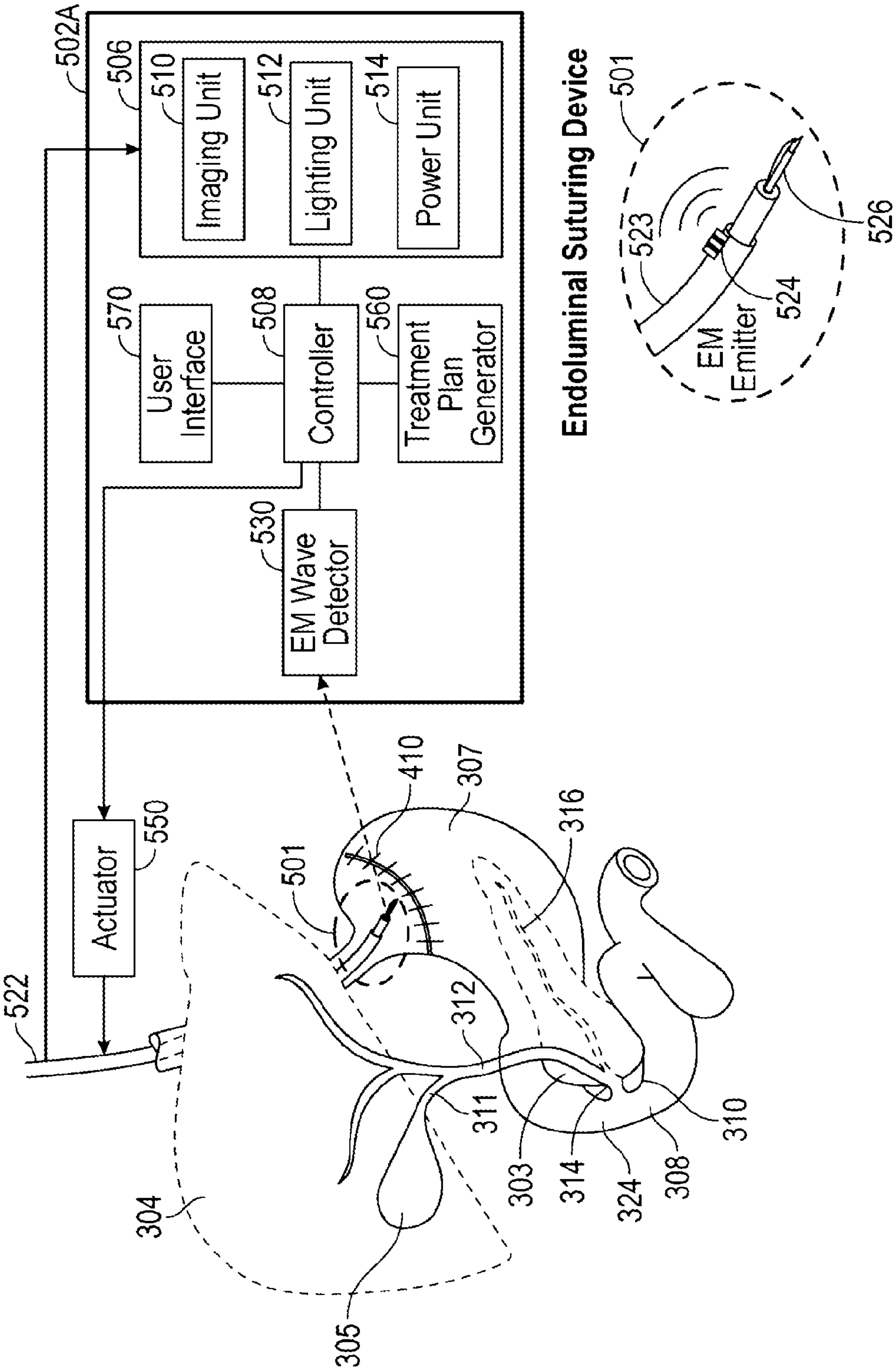
FIG. 5A illustrates an example of an alterable endoscopic gastric closure and a portion of a medical system used for the procedure.

FIG. 5A is a diagram illustrating an example of endoscopically creating an alterable gastric closure 410 (such as sutures as shown here and similarly in FIG. 4) and at least a portion of the medical system used for the procedure. A steerable elongate instrument 522 can be inserted into patient mouth, pass through the esophagus, and enter into an upper portion of the stomach 307. The steerable elongate instrument 522 may include at its distal end portion 501 a functional module 523 and a control module 506. The functional module 523 can support an endoluminal closing device 526 operably extendable from and retractable into the distal portion of the steerable elongate instrument 522. When the distal portion of the steerable elongate instrument 522 is determined to have reached a desired location of the upper stomach region (as to be discussed further below), the endoluminal closing device 526 can apply an alterable gastric closure (e.g., sutures) to reversibly divide a first gastric portion from a second gastric portion to create a reversible alteration of gastric anatomy, as described above. Although the alterable gastric closure 410 as shown in FIG. 5A is created endoscopically, this is by way of example and not limitation. Other surgical approaches (e.g., laparoscopic approach) may be used to create the alterable gastric closure 410 using a closing device associated with a surgical device other than the steerable elongate instrument 522, which are contemplated as within the scope of the present disclosure.

The control module 506 may include, or be coupled to, a controller 508 of an imaging and control system 502A. Similar to the discussion above with respect to FIG. 1, the control module 506 may include other components, such as those described with reference to endoscopy system 10 (FIG. 1) and control unit 16 (FIG. 2). Additionally, the control module 506 can comprise components for controlling an imaging device (e.g., a camera) and a light source connected to steerable elongate instrument 522, such as an imaging unit 510, a lighting unit 512 and a power unit 514. The imaging unit 512, which may include an imaging sensor or camera, can produce an endoscopic image of the upper portion of the stomach 307. The controller 508 can identify position and posture of the endoluminal closing device 526 from the endoscopic image. In an example, the functional module 523 may include an electromagnetic (EM) wave emitter 524 associated with or in proximity to the endoluminal closing device 526. The EM wave emitter 524 can emit EM waves, at least a portion of which can be detected transabdominally by an external EM wave detector 530 included in the imaging and control system 502A. The controller 508 can use at least the detected EM waves to identify the position and posture of the endoluminal closing device 526.

The endoscopic image of the portion of the stomach and the identified position and posture of the endoluminal closing device 526 can be presented to a user on a user interface 570. In an example, an interactive and navigable street view of an image of the reversibly altered gastric anatomy may be created and displayed on the user interface with distinct landmarks. The navigable street view allows a user to easily explore different areas in the field of view, zoom in or zoom out a landmark (e.g., an anatomical structure). In an example, under the street view, the user may use a pointing device to point to a landmark or a location further away in the distance, and by clicking on that landmark or location in the distance, the view updates and the current field of view is advanced towards that landmark or location. In some examples, along with the view update, the robotic surgical system can be instructed to automatically proceed toward that landmark or location. This simplifies the navigation process and reduces the technical and training burden on the operator by transferring these challenges to the robotic platform.

Information about the position and posture of the endoluminal closing device 526, such as based on the endoscopic image and/or the detected EM waves, may help guide an operator (e.g., endoscopist or an operating physician) to position the distal portion of the steerable elongate instrument 522 at a desired location of the upper stomach region where a reversible gastric anatomy alteration may be performed using the endoluminal closing device 526. In an example, the controller 508 may include, or be coupled to, a treatment plan generator 560. The treatment plan generator 560, which is an example of the treatment generator 44 as illustrated in FIG. 2, can automatically generate a treatment plan. The treatment plan may include, for example, information about identified closing site and closing trajectory on a portion of the stomach 307. The closing site and closing trajectory can be overlaid on the image of the stomach and presented to the operating physician. In some examples, the treatment plan generator 560 may include an artificial intelligence (AI)-based decision system that uses a trained computational model to identify the closing site and trajectory based at least in part on the image of the stomach 307. The treatment plan thus generated can be provided to the operator to guide the reversible gastric closure procedure. The operator can perform endoscopic suturing and keep the proper stomach shape from inside the GI lumen. In some examples, the treatment plan (including the identified closing site and trajectory) may be provided to a robotic surgical system that can robotically manipulate the endoluminal closing device 526 via an actuator 550 to perform the alterable gastric closure in accordance with the treatment plan. The treatment plan, including the closing site and trajectory, can be stored in a memory device. In some examples, such treatment plan may be retrieved from the memory and used to identify site and route to partially disengage the previously created alterable gastric closure, as described further below with reference to FIG. 5B.

In an example, the AI-based decision system can apply images or image features to a trained machine-learning (ML) model to identify the closing site and trajectory. The ML model 464 may be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations. In an example, the training of a ML model may include constructing a training dataset comprising image data, manipulation parameters of the endoluminal closing device, and the outcome of the procedure (e.g., success rate and patient complications) collected from past reversible gastric alteration procedures performed on a plurality of patients. The training involves algorithmically adjusting one or more ML model parameters, until the ML model being trained satisfies a specified training convergence criterion. The trained ML model can be validated, and implemented in the AI-based decision system to generate individualized treatment plan for the patient.

Figure 5B:
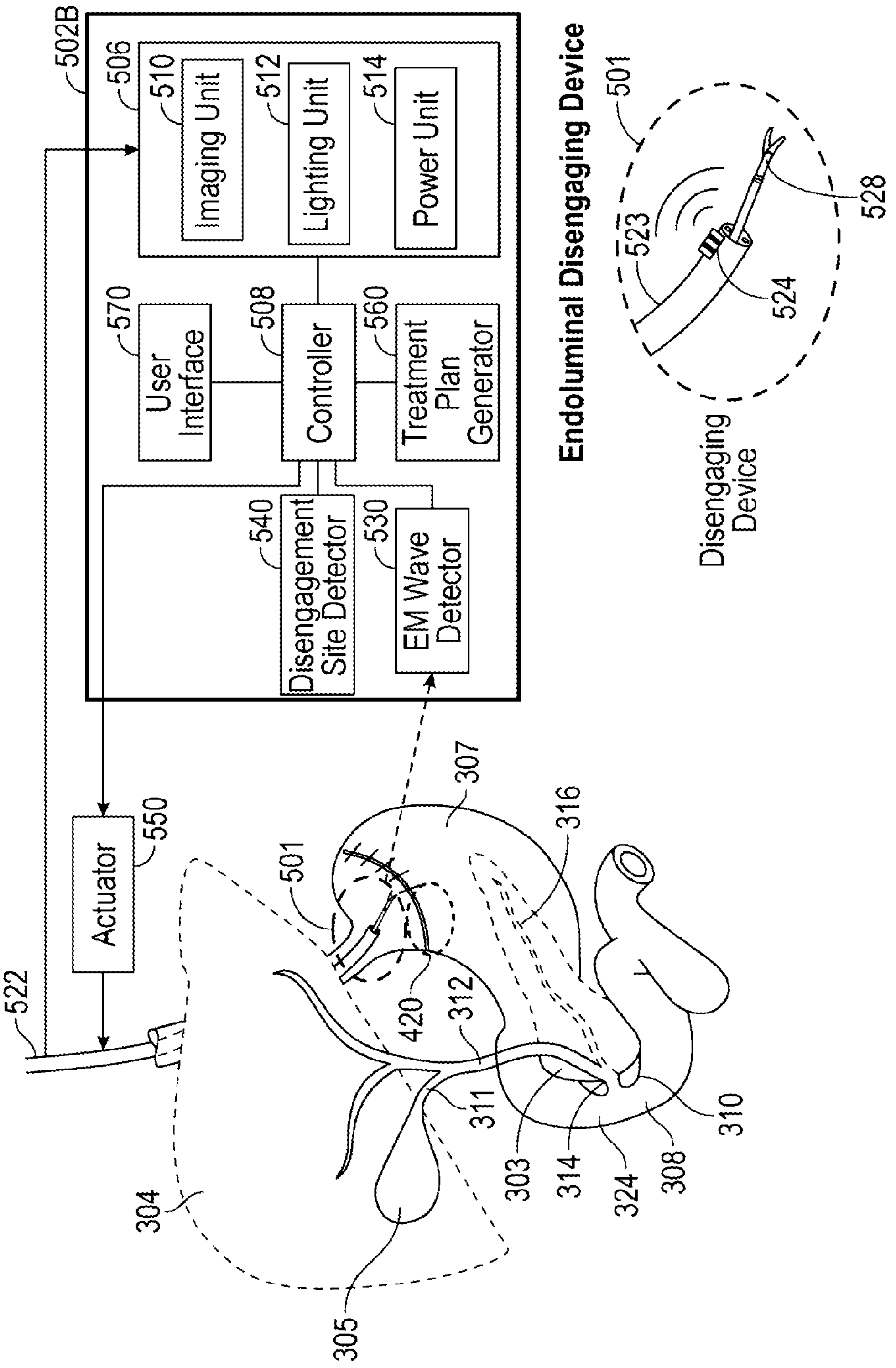
FIG. 5B illustrates an example of endoscopically creating at least a partial disengagement of the previously created alterable gastric closure and a portion of a medical system used for the procedure.

FIG. 5B is a diagram illustrating an example of endoscopically creating at least a partial disengagement of the previously created alterable gastric closure (such as the disengaged portion 420 of the gastric closure 410 shown in FIG. 4), and at least a portion of the medical system used for the procedure. As described in FIG. 4, the partial disengagement of the alterable gastric closure 410 can create an opening that at least partially reconnects the first and second gastric portions and allow an endoscope to pass through the stomach 307 and the duodenum 308, and reach the duodenal papilla 314 during the pancreaticobiliary endoscopic procedure. Similar to the reversible gastric closure as described above with reference to FIG. 5A, the steerable elongate instrument 522 can pass down to the upper portion of the stomach 307. The functional module 523 at the distal end portion 501 of steerable elongate instrument 522 can support an endoluminal disengaging device 528 operably extendable from and retractable into the distal portion of the steerable elongate instrument 522. When the distal portion of the steerable elongate instrument 522 is determined to be at a desired location of the upper stomach region and a proper disengagement site is identified (as to be discussed further below), the endoluminal disengaging device 528 can disengage at least a portion 420 of the alterable gastric closure 410, such that the first and second gastric portions can be at least partially reconnected, as described above with reference to FIG. 4. Although the disengagement portion 420 as shown in FIG. 5B is created endoscopically, this is by way of example and not limitation. Other surgical approaches (e.g., laparoscopic approach) may be used to create the disengagement portion 420 using a disengaging device associated with a surgical device other than the steerable elongate instrument 522, which are contemplated as within the scope of the present disclosure.

Similar to the imaging and control system 502A as shown in FIG. 5A, the imaging and control system 502B in FIG. 5B includes the control module 506 at the distal end portion 501 of steerable elongate instrument 522 coupled to the controller 508. The imaging unit 512 can produce an endoscopic image of the upper portion of the stomach 307. The controller 508 can identify position and posture of the endoluminal disengaging device 528 from the endoscopic image. The endoscopic image of the portion of the stomach and the identified position and posture of the endoluminal disengaging device 528 can be presented to a user on a user interface 570. Additionally or alternatively, as discussed above, an EM wave emitter 524 associated with or in proximity to the endoluminal disengaging device 528 can emit EM waves, at least a portion of which can be detected transabdominally by an EM wave detector 530 included in the imaging and control system 502B. The controller 508 use at least the detected EM waves to identify the position and posture of the endoluminal disengaging device 528.

Based on the image of the stomach and the identified position and posture of the endoluminal disengaging device 528A, a user input identifying disengaging site and trajectory can be received from the user interface. Alternatively, the imaging and control system 502B may include a disengagement site detector 540 configured to automatically determine the disengaging site and trajectory from the endoscopic image. The disengaging site and trajectory can be a portion of the closing site and trajectory when creating the reversibly altered gastric anatomy as shown in FIG. 5A. In some examples, the treatment plan created and stored for previous alterable gastric closure procedure may be retrieved from the memory and used to identify the disengagement site and trajectory. In some examples, a marker can be applied to at least a portion of the alterable gastric closure during the procedure of reversible alteration of gastric anatomy. During the disengagement procedure, the marker may be identified from the image, and the disengaging site and trajectory can be determined to be at or proximal to the identified marker. In some examples, the treatment plan generator 560 may include an AI-based decision system that uses a trained computational model (e.g., a trained ML model) to identify the disengagement site and trajectory based at least in part on the image of the stomach 307. The disengagement site and trajectory can be provided to the operator to guide the disengagement procedure. Additionally or alternatively, the disengagement site and trajectory may be provided to a robotic surgical system that can robotically manipulate the endoluminal disengaging device 528 via an actuator 550 to perform the partial gastric disengagement in accordance with the treatment plan.

The disengagement creates an opening at the disengaged portion 420 that at least partially reconnects previously separated first and second gastric portions. The steerable elongate instrument 522 can pass through said opening, the second gastric portion 414, and the duodenum 308, and perform diagnostic or therapeutic operations at the pancreaticobiliary anatomy.

Figure 6:
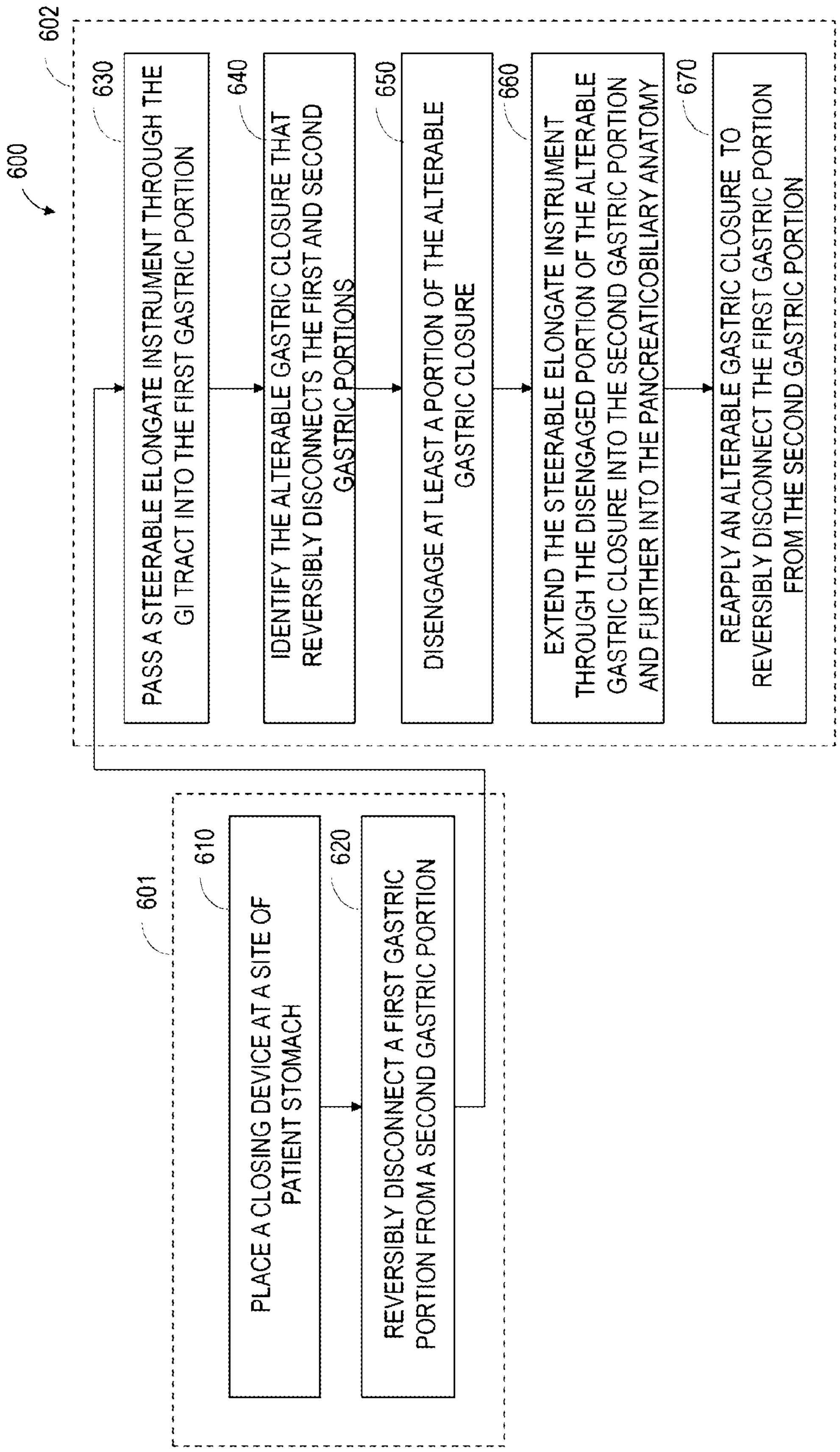
FIG. 6 is a flow chart illustrating an example method for endoluminal transgastric access to a pancreaticobiliary anatomy of a patient to perform diagnostic or therapeutic operations therein.

FIG. 6 is a flow chart illustrating an example method 600 for endoluminal transgastric access to a pancreaticobiliary anatomy of a patient to perform diagnostic or therapeutic operations therein. The method 600 comprises a first phase 601 of creating an alterable gastric closure (such as sutures as shown in FIGS. 4 and 5A), and a second phase 602 of creating a partial disengagement of the previously created alterable gastric closure (such as partial disengagement of the sutures as shown in FIGS. 4 and 5B). Although the first phase 601 and the second phase 602 are both included in method 600, said two phases can be separately executed, for example, as two separate procedures performed at different times (e.g., different days), and/or upon meeting respective different surgical criteria. For example, the first phase 601 can be executed when the patient is indicated for a bariatric (weight loss) procedure, and the second phase 602 can be executed when the alterable gastric closure has been created (e.g., in a previous procedure), and the patient is indicated for an ERCP procedure. The first phase 601 and the second phase 602 can be implemented in or executed using the imaging and control system 502A as shown in FIG. 5A or the imaging and control system 502B as shown in FIG. 5B, respectively.

The first phase 601 includes a step 610 of placing a closing device at a site of patient stomach, such as an endoluminal gastric site. The closing device can be associated with a surgical device, such as an endoscope (or other endoluminal instrument), or a laparoscope. In an example, the closing device is an endoluminal closing device 526 operably disposed at a distal portion of a steerable elongate instrument (e.g., an endoscope, such as the cholangioscope 324). The steerable elongate instrument can be passed through a portion of gastrointestinal (GI) tract. The steerable elongate instrument, such as the steerable elongate instrument 522, may include an endoscope with multiple luminal channels. The steerable elongate instrument can be inserted into patient mouth, pass through the esophagus, and enter into an upper portion of the stomach.

At step 620, a reversible alteration of gastric anatomy can be created, such as by reversibly disconnecting a first gastric portion from a second gastric portion using an alterable gastric closure the closing device. To facilitate creation of the alterable gastric closure, position and posture of the closing device (e.g., the endoluminal closing device 526) can be identified during the procedure, such as using the endoscopic image of the portion of the GI tract. Additionally or alternatively, the position and posture of the closing device can be identified using electromagnetic (EM) wave emitted from an EM emitter associated with the closing device and sensed by an EM sensor, such as the EM wave detector 530.

The endoscopic image of the portion of the stomach and the identified position and posture of the closing device can be presented to a user (e.g., the operating physician) on a user interface. In an example, an interactive and navigable street view of an image of the reversibly altered gastric anatomy may be created and displayed on the user interface with distinct landmarks. Using the endoscopic images and information about the position and posture of the endoluminal closing device, the use can be guided to position the distal portion of the steerable elongate instrument at a desired location of the upper stomach region where a reversible gastric anatomy alteration may be performed using the endoluminal closing device, such as using an endoscopic suturing device to suturing a portion of the stomach, thereby reversibly disconnecting a first gastric portion from a second gastric portion.

In some examples, the endoscopic image of the portion of the stomach and the identified position and posture of the endoluminal closing device can be used to generate a treatment plan that includes identified closing site and closing trajectory on a portion of the stomach. In an example, an AI-based computational model can be used to identify the closing site and trajectory and guide the reversible gastric closure procedure. The operating physician can perform endoscopic suturing and keep the proper stomach shape from inside the GI lumen. In some examples, the treatment plan (including the identified closing site and trajectory) may be provided to a robotic surgical system that can robotically manipulate the endoluminal closing device to perform the alterable gastric closure in accordance with the treatment plan. The treatment plan, including the closing site and trajectory, can be stored in a memory device.

The second phase 602 includes steps for performing an endoscopic procedure such as ERCP in surgically altered gastric anatomy such as created in phase 601. At 630, a steerable elongate instrument can be passed through a portion of the GI tract to the first gastric portion of the stomach that is surgically disconnected from the second gastric portion. At 640, the alterable gastric closure that reversibly disconnects the first and second gastric portions can be identified, such as from the endoscopic image taken during the procedure. In an example, a marker can be applied to at least a portion of the alterable gastric closure when creating the reversible alteration of gastric anatomy in the first phase 601. During the disengagement procedure in the second phase 602, the marker may be identified from the endoscopic image, and the disengaging site and trajectory can be determined to be at or proximal to the identified marker.

At 650, at least a portion of the identified alterable gastric closure can be disengaged using a disengaging device. The disengaging device can be associated with a surgical device, such as an endoscope (or other endoluminal instrument), or a laparoscope. In an example, the disengaging device can be the endoluminal disengaging device 528 disposed at a distal portion of the steerable elongate instrument. The disengagement at least partially reconnects the first and second gastric portions. To facilitate disengagement of the alterable gastric closure, position and posture of the endoluminal disengaging device can be identified using the endoscopic image of the portion of the GI tract. Additionally or alternatively, the position and posture of the endoluminal disengaging device can be identified using electromagnetic (EM) wave emitted from an EM emitter associated with the endoluminal disengaging device and sensed by an EM sensor, such as the EM wave detector 530.

The disengagement can be created at an identified disengaging site and/or along an identified disengaging trajectory. In an example, the disengaging site and trajectory can be designated by the user, based on the endoscopic image of the stomach and the identified position and posture of the endoluminal disengaging device. Alternatively, the disengaging site and trajectory can be automatically determined the disengaging site and trajectory from the endoscopic image. Disengaging site and trajectory can be a portion of the closing site and trajectory where the alterable gastric closure is applied when creating the reversibly altered gastric anatomy as shown in FIG. 5A. In some examples, a treatment plan including the disengaging site and trajectory can be determined using an AI-based computational model that takes the endoscopic image of the portion of the stomach and the identified position and the posture of the endoluminal disengaging device as input to the model. The disengagement site and trajectory can be provided to the operating physician to guide the disengagement procedure. Additionally or alternatively, the disengagement site and trajectory may be provided to a robotic surgical system that can robotically manipulate the endoluminal disengaging device via an actuator to perform the partial gastric disengagement in accordance with the treatment plan.

The disengagement creates an opening at the disengaged portion of the alterable gastric closure created at the first phase 601. The opening at least partially reconnects previously separated first and second gastric portions. At 660, the steerable elongate instrument can be extended through the opening of the disengaged portion into the second gastric portion and further into the pancreaticobiliary anatomy to perform diagnostic or therapeutic operation therein.

At 670, at a conclusion of the pancreaticobiliary endoscopy procedure, the endoscope can be retracted, an alterable gastric closure can be used to re-close the opening at the disengaged portion, as similarly described above with respect to step 620 of the first phase 601. The second gastric portion remains to be bypassed, and the bariatric (weight loss) treatment would not be affected. If and when the patient needs another pancreaticobiliary endoscopy procedure, some or all of the steps in the second phase 602 can be repeated to create a disengagement portion to allow the endoscope to pass therethrough and achieve transgastric access to the pancreaticobiliary system.

Figure 7:
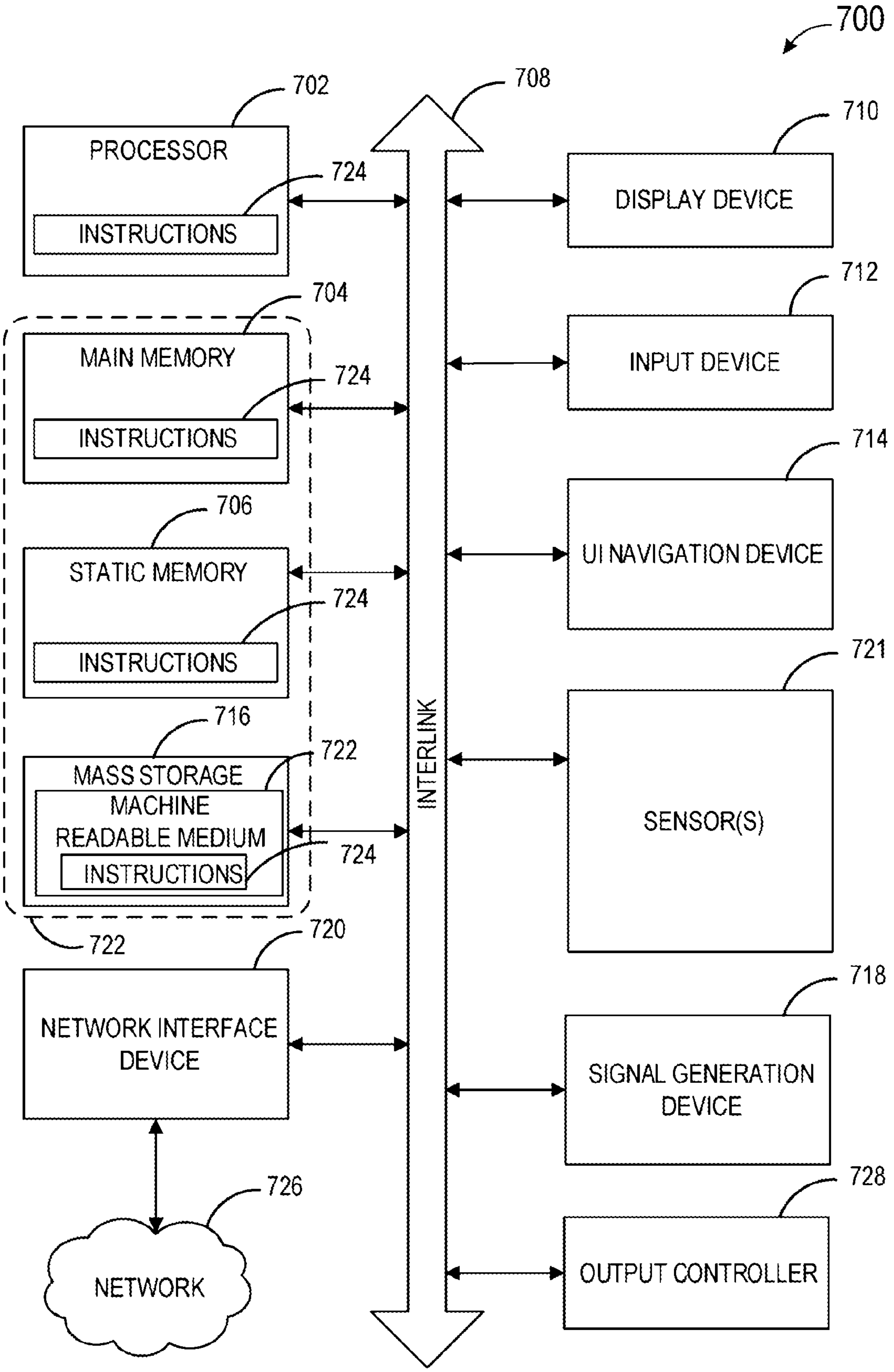
FIG. 7 is a block diagram illustrating an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the treatment plan generator 460, such as the AI-based access decision system 462.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

(1st aspect) A method for endoluminal transgastric access to a pancreaticobiliary anatomy of a patient, the method comprising:
- creating a reversible alteration of gastric anatomy in the patient, including reversibly disconnecting a first gastric portion from a second gastric portion using an alterable gastric closure and a closing device;
- during a pancreaticobiliary endoscopy procedure:
  - passing a steerable elongate instrument through a portion of gastrointestinal (GI) tract into the first gastric portion;
  - identifying the alterable gastric closure that reversibly disconnects the first and second gastric portions;
  - disengaging at least a portion of the alterable gastric closure using an endoluminal disengaging device operably disposed at a distal portion of the steerable elongate instrument, the disengagement at least partially reconnecting the first and second gastric portions; and
  - extending the steerable elongate instrument through the disengaged portion of the alterable gastric closure into the second gastric portion and further into the pancreaticobiliary anatomy to perform diagnostic or therapeutic operation therein.

(2nd aspect) The method of 1st aspect, further comprising, at a conclusion of the pancreaticobiliary endoscopy procedure, reapplying an alterable gastric closure to reversibly disconnect the first gastric portion from the second gastric portion using the closing device.

(3rd aspect) The method of 1st aspect, wherein the diagnostic or therapeutic operation includes an endoscopic cholangiopancreatography (ERCP) procedure or a direct peroral cholangioscopy (DPOC) procedure.

(4th aspect) The method of 1st aspect, wherein the first and second gastric portions are respectively a gastric pouch and an excluded stomach portion identified in a gastric bypass procedure.

(5th aspect) The method of 1st aspect, wherein reversibly disconnecting the first gastric portion from the second gastric portion includes using an endoluminal closing device operably disposed at a distal portion of the steerable elongate instrument.

(6th aspect) The method of 1st aspect, wherein the alterable gastric closure includes at least one of:
- alterable sutures;
- alterable glue; or
- alterable clips.

(7th aspect) The method of 1st aspect, comprising:
- identifying position and posture of one or more of the closing device or the endoluminal disengaging device; and
- providing the identified position and posture of one or more of the closing device or the endoluminal disengaging device to a user on a user interface, or to a robotic endoscopy system to facilitate robotic manipulation of the closing device or the endoluminal disengaging device.

(8th aspect) The method of 7th aspect, comprising receiving endoscopic image of the portion of the GI tract,
- wherein identifying the position and posture of one or more of the closing device or the endoluminal disengaging device is based at least on the received endoscopic image.

(9th aspect) The method of 7th aspect, comprising detecting electromagnetic (EM) wave emitted from an EM emitter associated with one or more of the closing device or the endoluminal disengaging device,
- wherein identifying the position and posture of one or more of the closing device or the endoluminal disengaging device is based at least on the detected EM waves.

(10th aspect) The method of 8th aspect, comprising:
- receiving from the user interface a user input identifying closing site and trajectory on the endoscopic image of the portion of the GI tract; and
  - robotically manipulating the closing device to apply the alterable gastric closure to the identified closing site and trajectory.

(11th aspect) The method of 8th aspect, comprising, when creating the reversible alteration of gastric anatomy:
- identifying position and posture of a laparoscopic device used in a gastric bypass procedure from the endoscopic image; and
- presenting the endoscopic image of the portion of the GI tract and the identified position and posture of the laparoscopic device to a user on a user interface.

(12th aspect) The method of 7th aspect, comprising:
- receiving an endoscopic image of the portion of the GI tract during the pancreaticobiliary endoscopy procedure;
- identifying disengaging site and trajectory in proximity to the alterable gastric closure from the received endoscopic image; and robotically manipulating the endoluminal disengaging device to disengage at least the portion of the alterable gastric closure from the identified disengaging site and trajectory.

(13th aspect) The method of 12th aspect, comprising receiving a user input identifying the disengagement site and trajectory from the endoscopic image.

(14th aspect) The method of 12th aspect, wherein identifying the disengaging site and trajectory includes detecting a marker on at least a portion of the alterable gastric closure being applied when creating the reversible alteration of gastric anatomy.

(15th aspect) The method of 1st aspect, comprising presenting on a user interface an interactive and navigable view of an image of the reversibly altered gastric anatomy with distinct landmarks.

(16th aspect) An endoscopic system comprising:

a steerable elongate instrument configured for transgastric access to a pancreaticobiliary anatomy of a patient through a portion of gastrointestinal (GI) tract;

a closing device configured to reversibly alter gastric anatomy including reversibly disconnecting a first gastric portion from a second gastric portion using an alterable gastric closure; and an endoluminal disengaging device operably disposed at a distal portion of the steerable elongate instrument, the endoluminal disengaging device configured to disengage at least a portion of the alterable gastric closure during a pancreaticobiliary endoscopy procedure and thereby at least partially reconnecting the first and second gastric portions to facilitate transgastric access to a pancreaticobiliary anatomy via the steerable elongate instrument.

(17th aspect) The endoscopic system of 16th aspect, wherein the closing device includes an endoluminal closing device operably disposed at a distal portion of the steerable elongate instrument.

(18th aspect) The endoscopic system of 16th aspect, wherein the alterable gastric closure includes at least one of:

alterable sutures;

alterable glue; or alterable clips.

(19th aspect) The endoscopic system of 16th aspect, comprising a controller circuit configured to:

identify position and posture of one or more of the closing device or the endoluminal disengaging device; and provide the identified position and posture of one or more of the closing device or the endoluminal disengaging device to a user on a user interface, or to a robotic endoscopy system to facilitate robotic manipulation of closing device or the endoluminal disengaging device.

(20th aspect) The endoscopic system of 19th aspect, wherein the steerable elongate instrument includes an endoscope configured to produce an endoscopic image of the portion of the GI tract, wherein the controller circuit is configured to identify the position and posture of one or more of the closing device or the endoluminal disengaging device based at least on the endoscopic image.

(21th aspect) The endoscopic system of 19th aspect, comprising:

an electromagnetic (EM) wave emitter associated with the closing device or the endoluminal disengaging device, the EM wave emitter configured to emit EM waves; and an external EM wave detector configured to detect the emitted EM waves, wherein the controller circuit is configured to identify the position and posture of one or more of the closing device or the endoluminal disengaging device based at least on the detected EM waves.

(22th aspect) The endoscopic system of 20th aspect, wherein the controller circuit is configured to:

receive from the user interface a user input identifying closing site and trajectory on the image of the portion of the GI tract; and generate a control signal to an actuator of a robotic system to robotically manipulate the closing device to apply the alterable gastric closure to the identified closing site and trajectory.

(23th aspect) The endoscopic system of 19th aspect, wherein the controller circuit is configured to:

receive an endoscopic image of the portion of the GI tract during the pancreaticobiliary endoscopy procedure;

identify disengaging site and trajectory in proximity to the alterable gastric closure from the received endoscopic image; and generate a control signal to an actuator of a robotic system to robotically manipulate the endoluminal disengaging device to disengage at least the portion of the alterable gastric closure from the identified disengaging site and trajectory.

(24th aspect) The endoscopic system of 23th aspect, wherein to identify the disengaging site and trajectory, the controller circuit is configured to receive from the user interface a user input identifying the disengagement site and trajectory from the endoscopic image.

(25th aspect) The endoscopic system of 23th aspect, wherein to identify the disengaging site and trajectory, the controller circuit is configured to automatically detect a marker on at least a portion of the alterable gastric closure being applied when creating the reversible alteration of gastric anatomy.

(26th aspect) The endoscopic system of 19th aspect, comprising a user interface configured to present an interactive and navigable view of an image of the reversibly altered gastric anatomy with distinct landmarks.

FIELD OF THE DISCLOSURE

The present document relates generally to endoscopy systems, and more particularly to systems and methods for automated endoscopic procedure planning in patients with altered anatomy.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region may include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct Per-Oral Cholangioscopy (DPOC) procedure. In DPOC, a slim endoscope (cholangioscope) can be inserted into patient mouth, pass through the upper gastrointestinal (GI) tract, and enter into the common bile duct for visualization, diagnosis, and treatment of disorders of the biliary and pancreatic ductal systems.

Diagnostic or therapeutic endoscopy such as ERCP and DPOC is generally performed via an endoluminal route in the upper GI tract. Some patients have surgical alterations of a portion of GI tract (e.g., stomach) or the pancreaticobiliary system. Surgically or non-surgically altered anatomy can be a clinical challenge for endoscopists to perform such procedures. Computer-assisted endoscopic procedure planning, such as identifying proper endoscopes or other diagnostic or therapeutic tools and guidance of navigating and manipulating such endoscopes or tools in altered anatomy are needed to ensure high procedure accuracy and success rate in such patients.

SUMMARY

The present disclosure recognizes several technological problems to be solved with conventional endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

Another challenge in conventional endoscopy is a high degree of variability of patient anatomy, especially patients with surgically or non-surgically altered or otherwise difficult anatomy. For example, in ERCP procedures, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. In another example, some patients have alternated papilla anatomy. With the duodenoscope designed to be stable in the duodenum, it can be more difficult to reach the duodenal papilla in surgically or non-surgically altered anatomy. Conventional endoscopy systems generally lack the capability of providing cannulation and endoscope navigation guidance based on patient's unique anatomy.

Anatomical post-surgical alterations of the upper gastrointestinal (GI) tract have been a clinical challenge for performing diagnostic and therapeutic endoscopy, especially when pancreaticobiliary diseases are involved. Esophagectomy, gastrectomy with various reconstructions and pancreaticoduodenectomy are among the most common surgeries causing upper GI tract alterations. GI post-surgical alteration anatomy may also represent for endoscopic ultrasound (EUS) a hurdle for pancreatic examination and tissue acquisition such as due to the difficulty in achieving adequate scans of the pancreas or the distal bile duct, while on the other, it could be insurmountable to achieve the papillary region or the bilioenteric anastomosis during standard ERCP.

Proper knowledge of the anatomical alterations has been fundamental to perform endoscopy in those patients. For example, Roux-en-Y-Gastric Bypass (RYGB) surgery is one of the most common bariatric surgeries for obesity patients. The RYGB is a gastric bypass procedure performed laparoscopically by the surgeon to divide the stomach into a smaller upper portion (gastric pouch) and a lower majority of the stomach using surgical titanium staples, where the gastric pouch is then surgically attached to a middle portion of the small intestine (e.g., jejunum), thereby bypassing the rest of the stomach and the duodenum (upper portion of the small intestine). The gastric pouch restricts the amount of food intake and absorption of fewer calories and nutrients from the food. Pancreaticobiliary endoscopy, such as ERCP, in post-RYGB patients depends on the knowledge of the anatomic alteration and physician operator's experience. Moreover, even experienced physicians may not be able to find the way to obtain adequate window, and to move an endoscope through an altered anatomy, especially when anastomotic reconstructions are unclear or particularly laborious.

Conventional endoscopy systems generally lack the capability of automatic endoscopic procedure planning, including identifying proper endoscopes and other diagnostic or therapeutic tools, and navigating, positioning, and manipulating such endoscopes or tools, particularly in patients with altered anatomy such as surgically altered upper GI tract anatomy in an ERCP procedure. The operating physician generally positions and navigates the endoscope manually based on real-time endoscopic images and fluoroscopy images and their experience. This generally requires extensive training and experience over years, and can be challenging for inexperience physicians, especially in patients with difficult or surgically altered anatomy, as discussed above. The lack of automated endoscopic procedure planning based on patients unique anatomy particularly surgically altered anatomy may reduce procedure accuracy, efficiency, and success rate.

The present disclosure can help solve these and other problems by providing a computer-assisted, image-based endoscopic procedure planning system and method of using such system in patients with altered anatomy, such as surgically altered upper GI tract. According to one aspect of the present disclosure, an endoscopy planning system comprises a processor that can receive preoperative images of at least a portion of an altered anatomy, such as a surgically or non-surgically altered stomach or other parts of the upper GI tract, analyze the preoperative images to generate an endoscopy plan including to determine an navigation route through the altered anatomy toward a target portion in the preoperative images. The endoscopy plan can be presented to a user on a user interface, or provided to a robotic endoscopy system to facilitate robot-assisted procedure.

Example 1 is an endoscopy planning system, comprising: a processor configured to: receive preoperative images of at least a portion of a surgically altered anatomy; generate an endoscopy plan using the received preoperative images, including determine a navigation route through the surgically altered anatomy toward a target portion in the preoperative images; and output the endoscopy plan to a user or a robotic endoscopy system to perform an endoscopy procedure in accordance with the endoscopy plan.

In Example 2, the subject matter of Example 1 optionally includes, wherein the processor is configured to select an endoscope or to determine the navigation route by applying at least one trained machine-learning model to the received preoperative images.

In Example 3, the subject matter of any one or more of Examples 1-2 optionally include, wherein the preoperative images include one or more of: a fluoroscopic image; a computer-tomography (CT) scan image; a magnetic resonance imaging (MRI) scan image; an electrical potential map or an electrical impedance map; a magnetic resonance cholangiopancreatography (MRCP) image; or an endoscopic ultrasonography (EUS) image.

In Example 4, the subject matter of any one or more of Examples 1-3 optionally include, wherein the preoperative images include one or more endoscopic images from prior endoscopic procedures.

In Example 5, the subject matter of any one or more of Examples 1-4 optionally include, wherein the processor is configured to: recognize an anatomical structure and determine one or more positional or geometric parameters of the recognized anatomical structure from the received preoperative images; and generate the endoscopy plan further using the one or more positional or geometric parameters of the recognized anatomical structure.

In Example 6, the subject matter of Example 5 optionally includes, wherein the processor is configured to apply at least one trained machine-learning model to the received preoperative images to recognize the anatomical structure or determine the one or more positional or geometric parameters.

In Example 7, the subject matter of any one or more of Examples 1-6 optionally include, wherein to generate the endoscopy plan further includes to select an endoscope with a recommended type, size, or length.

In Example 8, the subject matter of Example 7 optionally includes, wherein the surgically altered anatomy includes an altered gastrointestinal (GI) tract, and wherein the endoscopy plan is with regard to passing the selected endoscope through the altered GI tract into an pancreaticobiliary anatomy.

In Example 9, the subject matter of Example 8 optionally includes a user interface configured to receive a user input designating, on at least one of the preoperative images, a starting point and an end point on the altered GI tract for passing the selected endoscope, wherein the processor is configured to select the endoscope and to determine the navigation route further based on the starting point and the end point of the altered GI tract.

In Example 10, the subject matter of any one or more of Examples 8-9 optionally include, wherein the processor is configured to: determine one or more positional or geometric parameters of the altered GI tract from the received preoperative images of the altered GI tract; and generate the endoscopy plan including selecting the endoscope based at least on the determined one or more positional or geometric parameters of the altered GI tract.

In Example 11, the subject matter of Example 10 optionally includes, wherein the one or more positional or geometric parameters of the altered GI tract includes an estimated length of the navigation route for passing the selected endoscope in the altered GI tract, wherein the processor is configured to determine the selected endoscope of a particular length based on the estimated length of the navigation route.

In Example 12, the subject matter of any one or more of Examples 10-11 optionally include, wherein the one or more positional or geometric parameters of the altered GI tract includes an estimated angle between the navigation route and a target duct of the pancreaticobiliary anatomy into which the selected endoscope is to reach, wherein the processor is configured to determine the selected endoscope between a forward-viewing endoscope and a side-viewing endoscope based on the estimated angle between the navigation route and the target duct.

In Example 13, the subject matter of any one or more of Examples 1-12 optionally include, wherein the endoscopy plan includes recommended values of one or more operational parameters for operating an endoscope or for manipulating a surgical tool associated therewith during the endoscopy procedure.

In Example 14, the subject matter of Example 13 optionally includes, wherein the one or more operational parameters include a position, a posture, a heading direction, or an angle for the endoscope or the surgical tool.

In Example 15, the subject matter of any one or more of Examples 1-14 optionally include, wherein the processor is configured to receive preoperative images of a non-surgically altered anatomy, wherein to generate the endoscopy plan includes to determine the navigation route along at least a portion of a gastrointestinal tract toward a target portion in the preoperative images of the non-surgically altered anatomy.

Example 16 is a method of planning an endoscopy procedure in a surgically altered anatomy, the method comprising: receiving preoperative images of at least a portion of the surgically altered anatomy; generating an endoscopy plan using the received preoperative images, including determining a navigation route through the surgically altered anatomy toward a target portion in the preoperative images; and providing the endoscopy plan to a user or a robotic endoscopy system for use in the endoscopy procedure in accordance with the endoscopy plan.

In Example 17, the subject matter of Example 16 optionally includes, wherein generating the endoscopy plan includes applying the received preoperative images to at least one trained machine-learning model to determine the navigation route.

In Example 18, the subject matter of any one or more of Examples 16-17 optionally include: recognizing an anatomical structure and determining one or more positional or geometric parameters of the recognized anatomical structure from the received preoperative images; and generating the endoscopy plan further using the one or more positional or geometric parameters of the recognized anatomical structure.

In Example 19, the subject matter of Example 18 optionally includes applying at least one trained machine-learning model to the received preoperative images to recognize the anatomical structure or to determine the one or more positional or geometric parameters.

In Example 20, the subject matter of any one or more of Examples 16-19 optionally include, wherein generating the endoscopy plan includes selecting an endoscope with a recommended type, size, or length.

In Example 21, the subject matter of Example 20 optionally includes, wherein the surgically altered anatomy includes an altered gastrointestinal (GI) tract, and wherein the endoscopy plan is with regard to passing the selected endoscope through the altered GI tract into an pancreaticobiliary anatomy.

In Example 22, the subject matter of Example 21 optionally includes receiving a user input designating, on at least one of the preoperative images, a starting point and an end point on the altered GI tract for passing the selected endoscope, wherein generating the endoscopy plan includes selecting the endoscope and determining the navigation route further based on the starting point and the end point of the altered GI tract.

In Example 23, the subject matter of any one or more of Examples 21-22 optionally include determining one or more positional or geometric parameters of the altered GI tract from the received preoperative images of the altered GI tract, wherein generating the endoscopy plan includes selecting the endoscope based at least on the determined one or more positional or geometric parameters of the altered GI tract.

In Example 24, the subject matter of Example 23 optionally includes, wherein the one or more positional or geometric parameters of the altered GI tract includes an estimated length of the navigation route for passing the selected endoscope in the altered GI tract, wherein generating the endoscopy plan includes determining an endoscope length based on the estimated length of the navigation route.

In Example 25, the subject matter of any one or more of Examples 23-24 optionally include, wherein the one or more positional or geometric parameters of the altered GI tract includes an estimated angle between the navigation route and a target duct of the pancreaticobiliary anatomy into which the selected endoscope is to reach, wherein generating the endoscopy plan includes selecting between a forward-viewing endoscope and a side-viewing endoscope based on the estimated angle between the navigation route and the target duct.

In Example 26, the subject matter of any one or more of Examples 16-25 optionally include receiving preoperative images of a non-surgically altered anatomy, wherein generating the endoscopy plan includes determining the navigation route along at least a portion of a gastrointestinal tract toward a target portion in the preoperative images of the non-surgically altered anatomy.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

This document describes systems, devices, and methods for computer-assisted, image-based endoscopic procedure planning in patients with altered anatomy such as surgical alterations of upper GI tract. According to one embodiment, an endoscopy planning system comprises a processor that can receive preoperative images of an altered anatomy of at least a portion of a surgically altered anatomy through which an endoscope is to pass, analyze the preoperative images to generate an endoscopy plan, including to select an endoscope of a particular type or sizes, and to determine an navigation route for passing the selected endoscope through the altered anatomy. The endoscopy plan can be presented to a user on a user interface, or provided to a robotic endoscopy system to facilitate robot-assisted procedure.

Figure 8:
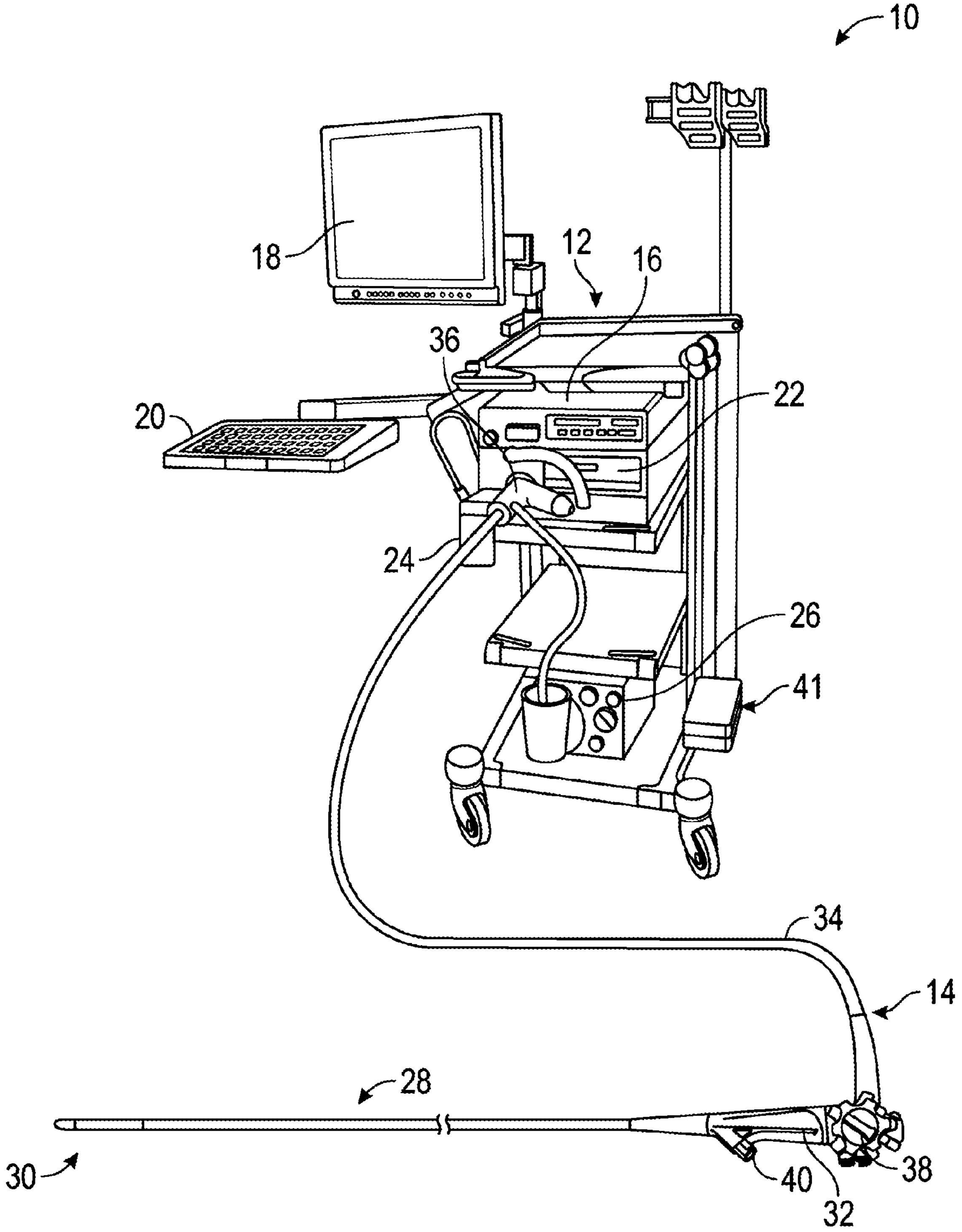
FIGS. 8 and 9 are schematic diagrams illustrating an example of an endoscopy system for use in endoscopic procedures such as an ERCP procedure.

FIG. 8 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 may include various ports for coupling with endoscopy system 10. For example, the control unit 16 may include a data input/output port for receiving data from and communicating data to the endoscope 14. The light source 22 may include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by an operator of endoscopy system 10 to control functions of endoscopy system 10 and view output of the endoscope 14. In some examples, the control unit 16 can additionally be used to generate signals or other outputs for treating the anatomical region into which the endoscope 14 is inserted. Examples of such signals or outputs may include electrical output, acoustic output, a radio-frequency energy output, a fluid output and the like for treating the anatomical region with, for example, cauterizing, cutting, freezing and the like.

The endoscope 14 can interface with and connect to the imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

Figure 12:
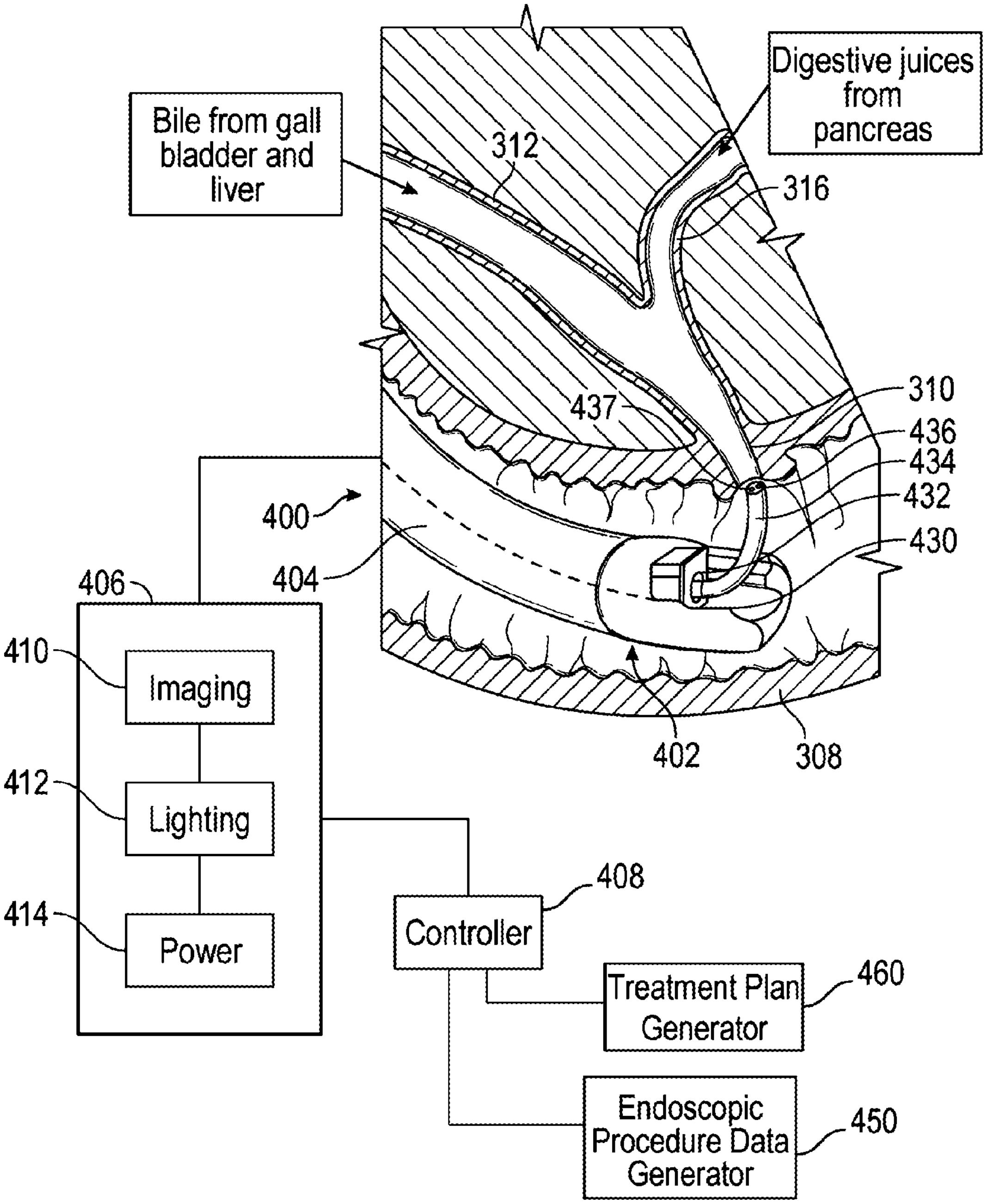
FIG. 12 illustrates an example of mother-daughter endoscopes used in an ERCP procedure, and a portion of patient anatomy where the procedure is performed.

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope as shown in FIG. 12. The working channel can extend between handle section 32 and functional section 30. Additional functionalities, such as fluid passages, guide wires, and pull wires can also be provided by insertion section 28 (e.g., via suction or irrigation passageways, and the like).

The handle section 32 can comprise a control knob 38 and ports 40. The ports 40 can be configured to couple various electrical cables, guide wires, auxiliary scopes, tissue collection devices of the present disclosure, fluid tubes and the like to handle section 32 for coupling with insertion section 28. The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 9) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 9), etc. Alternatively, several components of the imaging and control system 12 shown in FIGS. 8 and 9 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

Figure 9:
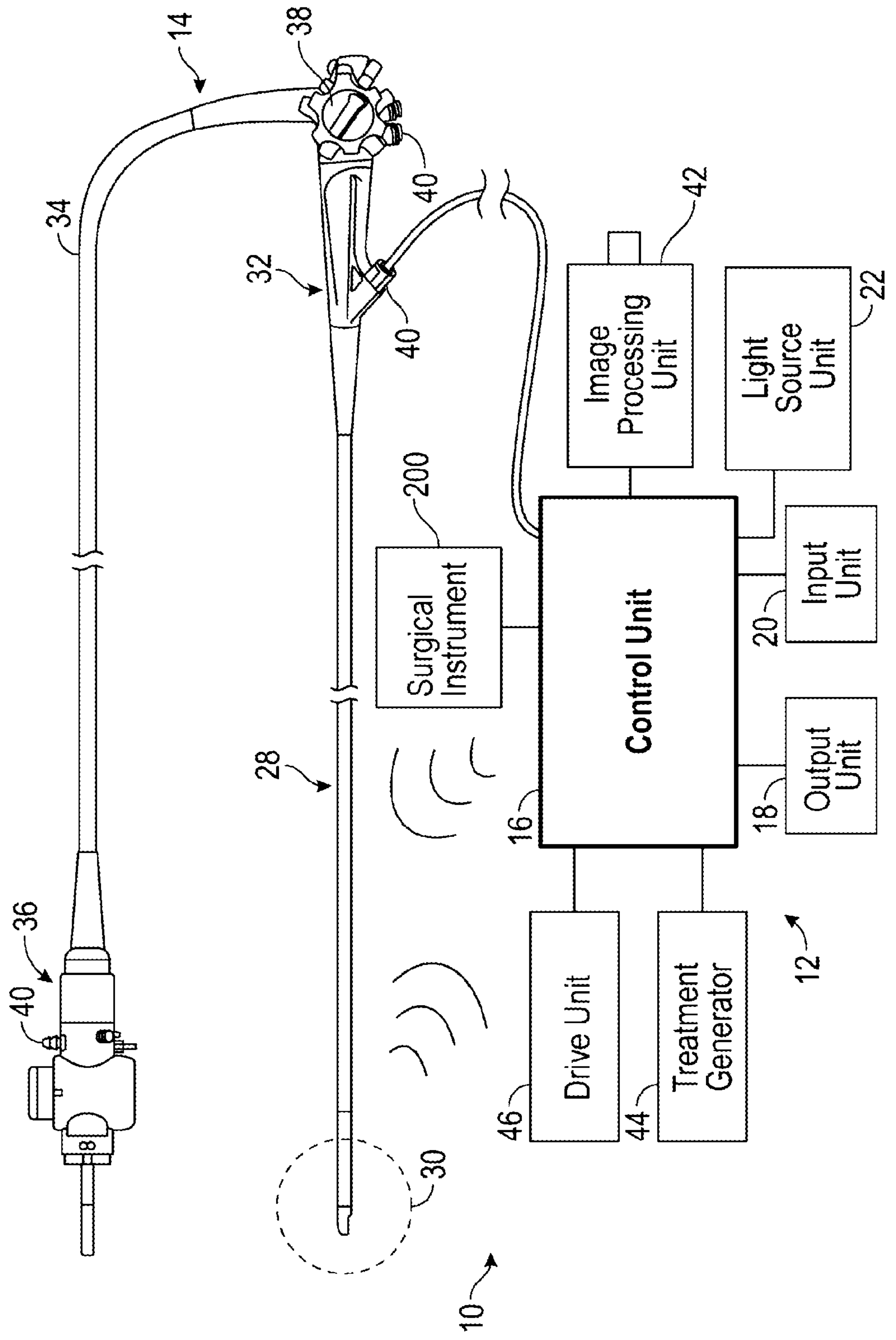
Figure 10:
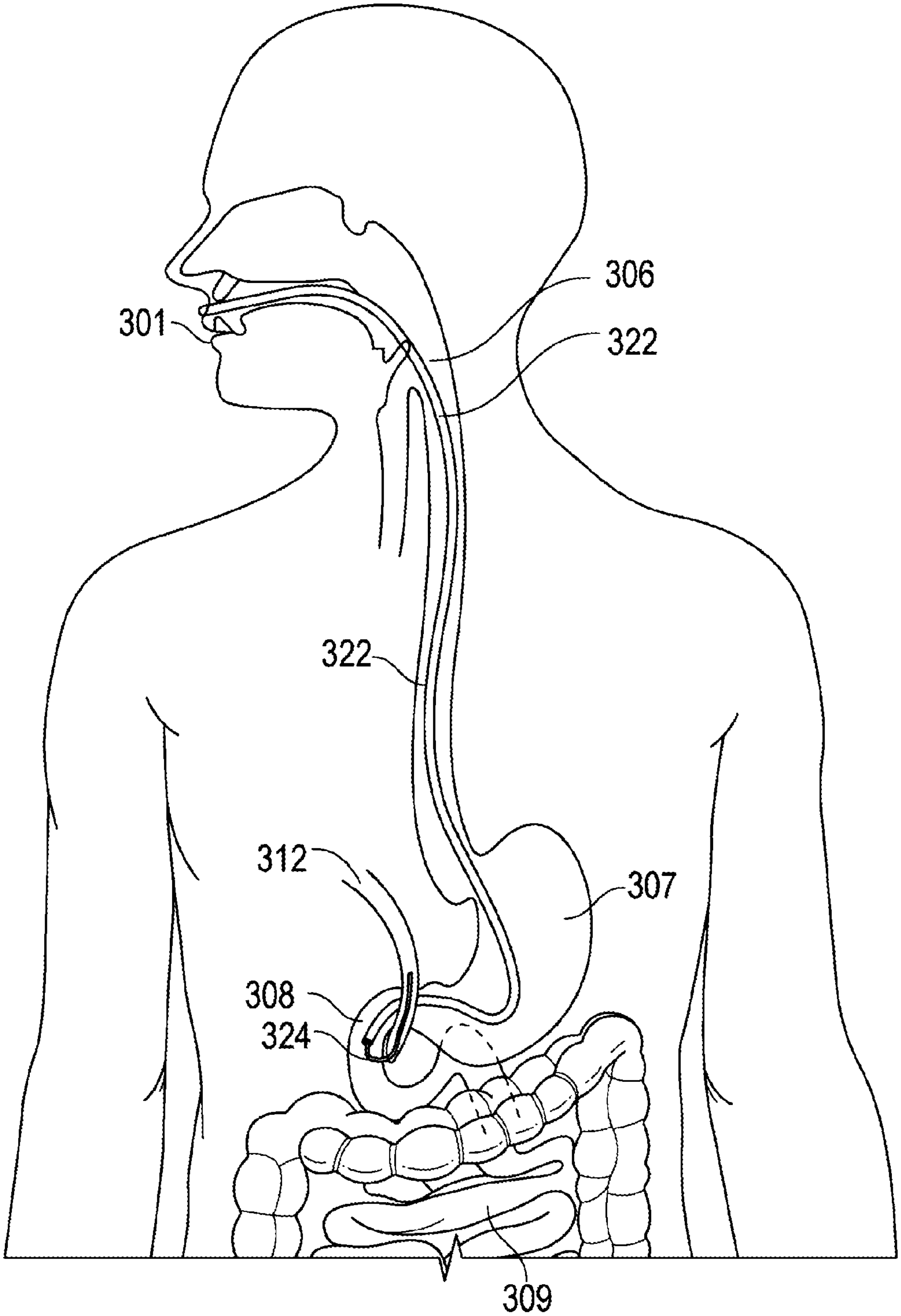
FIGS. 10 and 11 illustrate an example of peroral cholangioscopy involving direct insertion of a cholangioscope into patient bile duct as in a DPOC procedure, and a portion of patient anatomy where the procedure is performed.

FIG. 9 is a schematic diagram of the endoscopy system 10 shown in FIG. 8, which comprises the imaging and control system 12 and the endoscope 14. FIG. 9 schematically illustrates components of the imaging and control system 12 coupled to the endoscope 14, which in the illustrated example comprises a duodenoscope. The imaging and control system 12 can comprise a control unit 16, which may include or be coupled to an image processing unit 42, a treatment generator 44, and a drive unit 46, as well as the light source 22, the input unit 20, and the output unit 18 as discussed above with reference to FIG. 8. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which may include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 may include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

In some examples, the image processing unit 42 can reconstruct a 3D image using two or more images of an anatomical target, such as two or more 2D images. The 2D images can be from the same or different sources with the same or different modalities, which may include, for example, a fluoroscopic image, and an endoscopic image generated by the imaging device (e.g., a camera) on the endoscope 14. In some examples, at least some of the 2D images used for reconstructing the 3D image can be of the same modality. To reconstruct a 3D image, the image processing unit 42 may register a first 2D image to a second 2D image with respect to respective landmarks on the first and second 2D images, and apply a plurality of registered 2D images to a reconstruction model to create a 3D image. In some examples, the two or more images used for reconstructing the 3D image may include at least one existing 3D image obtained by using, for example, an external imaging device of equipment, such as a CT scanner, an MRI scanner, X-ray equipment, or a nuclear-medicine camera, among others. For example, the image processing unit 42 can reconstruct a 3D image using at least one 2D image and at least one existing 3D image, or in another example, using at least two existing 3D images.

In some examples, the image processing unit 42 can integrate the reconstructed 3D image with one or more secondary images generated by external imaging devices other than endoscope. Examples of the secondary images may include a CT image, an MRI image or an image obtained from specialized MRI such as a Magnetic resonance cholangiopancreatography (MRCP) procedure, or an endoscopic ultrasonography (EUS) image. Such images are referred to as secondary images to distinguish from images from primary sources such as endoscopic images.

The treatment generator 44 can generate a treatment plan, which can be used by the control unit 16 to control the operation of the endoscope 14, or to provide with the operating physician a guidance for maneuvering the endoscope 14, during an endoscopic procedure. In an example, the treatment plan may include an endoscope navigation plan for maneuvering the endoscope 14 in a surgically altered anatomy. The endoscope navigation plan can be generated based on patient information including an image of the surgically altered anatomy, and including estimated values for one or more cannulation or navigation parameters (e.g., an angle, a force, etc.). In an example, the endoscope navigation plan can be generated using preoperative images of non-surgically altered anatomy. The endoscope navigation plan can include a navigation route along at least a portion of the GI tract toward a target portion in the preoperative images of the non-surgically altered anatomy. The endoscope navigation plan can help guide the operating physician to cannulate and navigate the endoscope in the patient anatomy. The endoscope navigation plan may additionally or alternatively be used to robotically adjust the position, angle, force, and/or navigation of the endoscope or other instrument. Examples of endoscope navigation plan and robotic positioning and navigation in an endoscopic procedure are discussed below with reference to FIG. 14.

Figure 11:
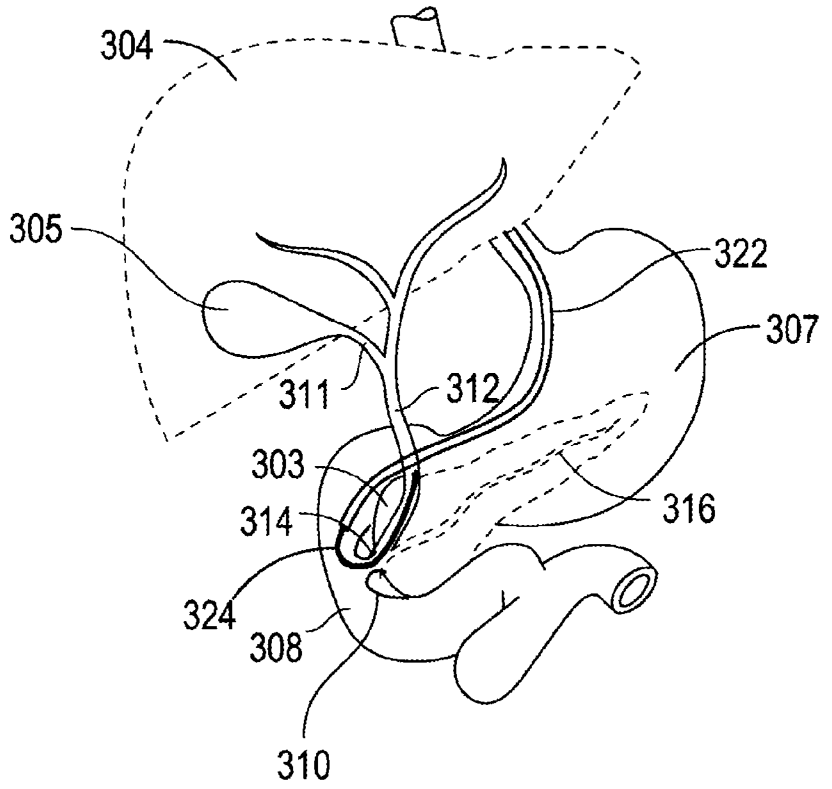

FIGS. 11A-11B are diagrams illustrating an example of peroral cholangioscopy performed via direct insertion of a cholangioscope 324 into the bile duct, as in a DPOC procedure, and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310 (FIG. 11B). The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

FIG. 11B is a schematic view of duodenum 308 connected to common bile duct 312 via duodenal papilla 314. Common bile duct 312 can branch off into pancreatic duct 316 and gallbladder duct 311. Duodenal papilla 314 may include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it is common during medical procedures to cut sphincter of Oddi 310 to enlarge duodenal papilla 314 to allow for easier access of instrument into common bile duct 312.

FIG. 12 is a diagram illustrating an example of mother-daughter endoscopes used in an ERCP procedure, and a portion of patient anatomy where the procedure is performed. The mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 may include, or be coupled to, a controller 408. Similar to the discussion above with respect to FIG. 8, the control module 406 may include other components, such as those described with reference to endoscopy system 10 (FIG. 8) and control unit 16 (FIG. 9). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 1 and 2.

The functional module 402 of the main scope 400 can comprise an elevator portion 430. The auxiliary scope 434 can itself include functional components, such as camera lens 437 and a light lens (not illustrated) coupled to control module 406, to facilitate navigation of the auxiliary scope 434 from the main scope 400 through the anatomy and to facilitate viewing of components extending from lumen 432.

In ERCP, the auxiliary scope 434 can be guided into the sphincter of Oddi 310. Therefrom, a surgeon operating the auxiliary scope 434 can navigate the auxiliary scope 434 through the lumen 432 of the main scope toward the gallbladder 305, liver 304, or other locations in the gastrointestinal system to perform various procedures. In some examples, the auxiliary scope 434 can be used to guide an additional device to the anatomy to obtain biological matter (e.g., tissue), such as by passage through or attachment to lumen 436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 400 and the auxiliary scope 434) may include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 408 may include, or be coupled to, an endoscopic procedure data generator 450, and a treatment plan generator 460. The endoscopic procedure data generator 450 can receive preoperative or perioperative images of surgically altered anatomy and its surrounding environment from external imaging devices. Such preoperative images can be of different modalities, such as X-ray or fluoroscopy images, electrical potential map or an electrical impedance map, computer tomography (CT) images, magnetic resonance imaging (MRI) images such as those obtained from Magnetic resonance cholangiopancreatography (MRCP), ultrasound images or endoscopic ultrasound (EUS) images, among others. In addition or alternative to the preoperative images, the endoscopic procedure data generator 450 can generate perioperative images of the surgically altered anatomy taken by imaging sensors associated with the endoscope during an endoscopy procedure, such as perioperative optical endoscopic images by an camera or optical imaging sensor and/or perioperative EUS images produced by an ultrasound transducer during an echoendoscopy procedure. The endoscopic procedure data generator 450 may additionally generate or receive other procedure-related information, including sensor information (e.g., sensors associated with the endoscope or with a treatment device passing through the endoscope), device information, patient medical history etc. In some examples, the endoscopic procedure data generator 450 can retrieve, such as from a database, stored control log data (e.g., time-series data) of past endoscopic procedures performed by a plurality of physicians on a plurality of patients. The control log data can represent preferred cannulation and endoscope navigation approaches and habits of physicians with different experience levels.

The treatment plan generator 460, which is an example of the treatment generator 44 as illustrated in FIG. 9, can automatically generate a treatment plan, such as an endoscope navigation plan for maneuvering an endoscope in a surgically altered anatomy. The endoscope navigation plan can be generated based on patient information including an image of the surgically altered anatomy, optionally along with other information produced by the endoscopic procedure data generator 450. The endoscope navigation plan may include one or more cannulation or navigation parameters with respective values. By way of example and not limitation, the cannulation or navigation parameters may include a position of the endoscope distal portion (e.g., the functional section 30 of the endoscope 14 as shown in FIG. 8) relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, among others, or a projected navigation path toward the anatomical target of interest, among others. According to various examples, the endoscope navigation plan (including, for example, cannulation or navigation parameters values) can be generated or updated using a trained machine-learning (ML) model as further described below. The endoscope navigation plan may be presented to the operating physician as a procedure guide.

Figure 13A:
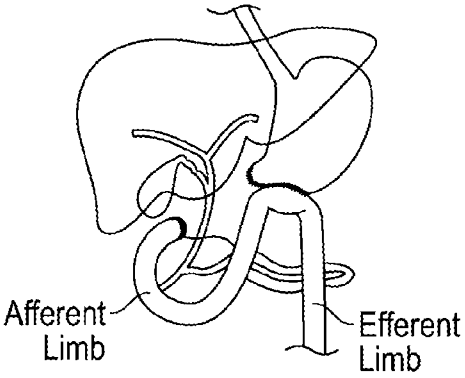
FIGS. 13A-13F illustrate various types of surgically altered anatomy of an upper GI tract.
Figure 13B:
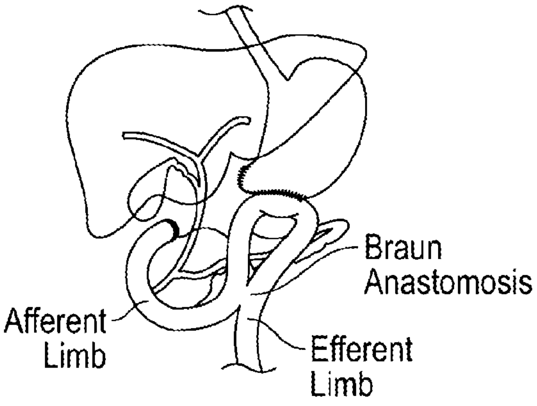
Figure 13C:
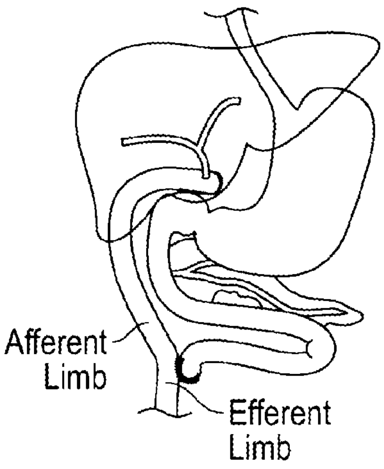
Figure 13D:
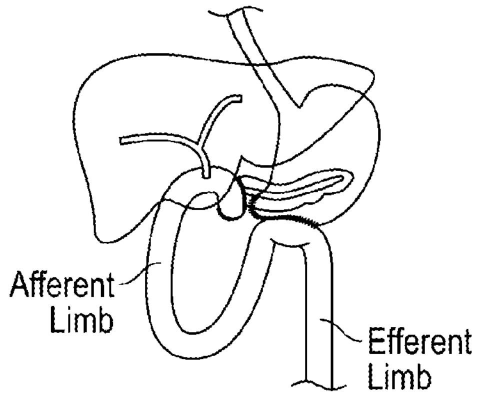
Figure 13E:
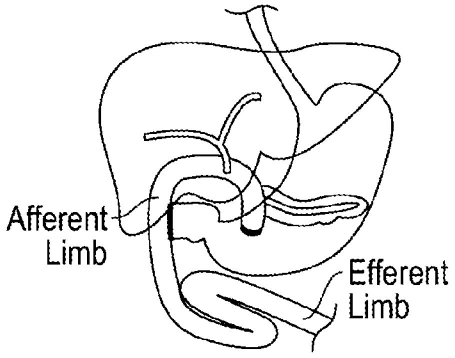
Figure 13F:
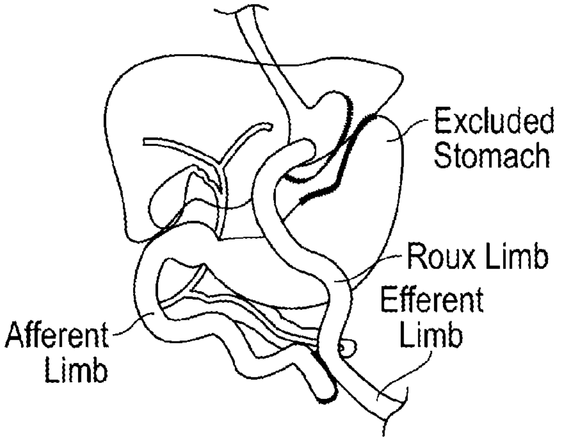

FIGS. 13A-13F are examples of surgically altered anatomy of an upper GI tract. FIG. 13A illustrates portions of GI anatomy post Billroth II gastrectomy. FIG. 13B illustrates portions of GI anatomy post a Braun variation of Billroth II, where a side-to-side jejunojejunostomy is created between the afferent and efferent limbs to divert bile from the gastric stump. This may create confusion regarding which enteral limb the endoscope is traversing. The operation may result in sharp luminal angulations and a longer afferent limb. FIG. 13C illustrates portions of GI anatomy post Roux-en-Y hepaticojejunostomy. A bilioenteric anastomosis is created at the end of a Roux limb leading from a jejunojejunostomy. The jejunojejunal anastomosis usually is encountered just distal to the ligament of Treitz. If the biliary anastomosis is performed above the bile duct confluence, more than one biliary opening may be encountered endoscopically, corresponding to the right and left main ducts at the hepaticojejunal anastomoses. FIGS. 13D and 13E illustrate respectively portions of GI anatomy post two main variations of pancreaticoduodenectomy: the classic Whipple (FIG. 13D) and the pylorus-preserving Whipple (FIG. 13E). The length of the afferent limb varies but in general is approximately 40 to 60 cm. The choledochojejunal anastomosis usually is about 10 cm proximal to the pancreaticojejunal anastomosis in the afferent limb. FIG. 13F illustrates portions of GI anatomy post Roux-en-Y gastric bypass (RYGB). Laparoscopic RYGB is one of the most commonly performed weight loss surgeries.

Several approaches can be used to perform ERCP in patients with altered GI anatomy, depending on the severity of illness and indication of procedure. Common approaches include peroral ERCP by using enteroscopes, surgically assisted ERCP, or percutaneous transgastric ERCP. The success of ERCP in patients with surgically altered anatomy depends on multiple factors including the postoperative anatomy, expertise of the endoscopist, and availability of specialized endoscopes and devices to perform endotherapy. For example, peroral ERCP with enteroscopes in RYGB anatomy can be especially challenging for several reasons. Reaching the papilla may be difficult because of potentially long Roux limbs, sharp luminal angulations, adhesions, internal hernias, and looping. Cannulating the major papilla from a caudal approach creates challenges in achieving adequate orientation. Additionally, the lack of an elevator limits control of the cannulation device. Furthermore, the array of ERCP accessory devices compatible with long-length enteroscopes is limited. Various embodiments as described in the present document provide computer-assisted, image-based endoscopic procedure planning which can improve the success rate of ERCP in surgically altered GI anatomy.

Figure 14:
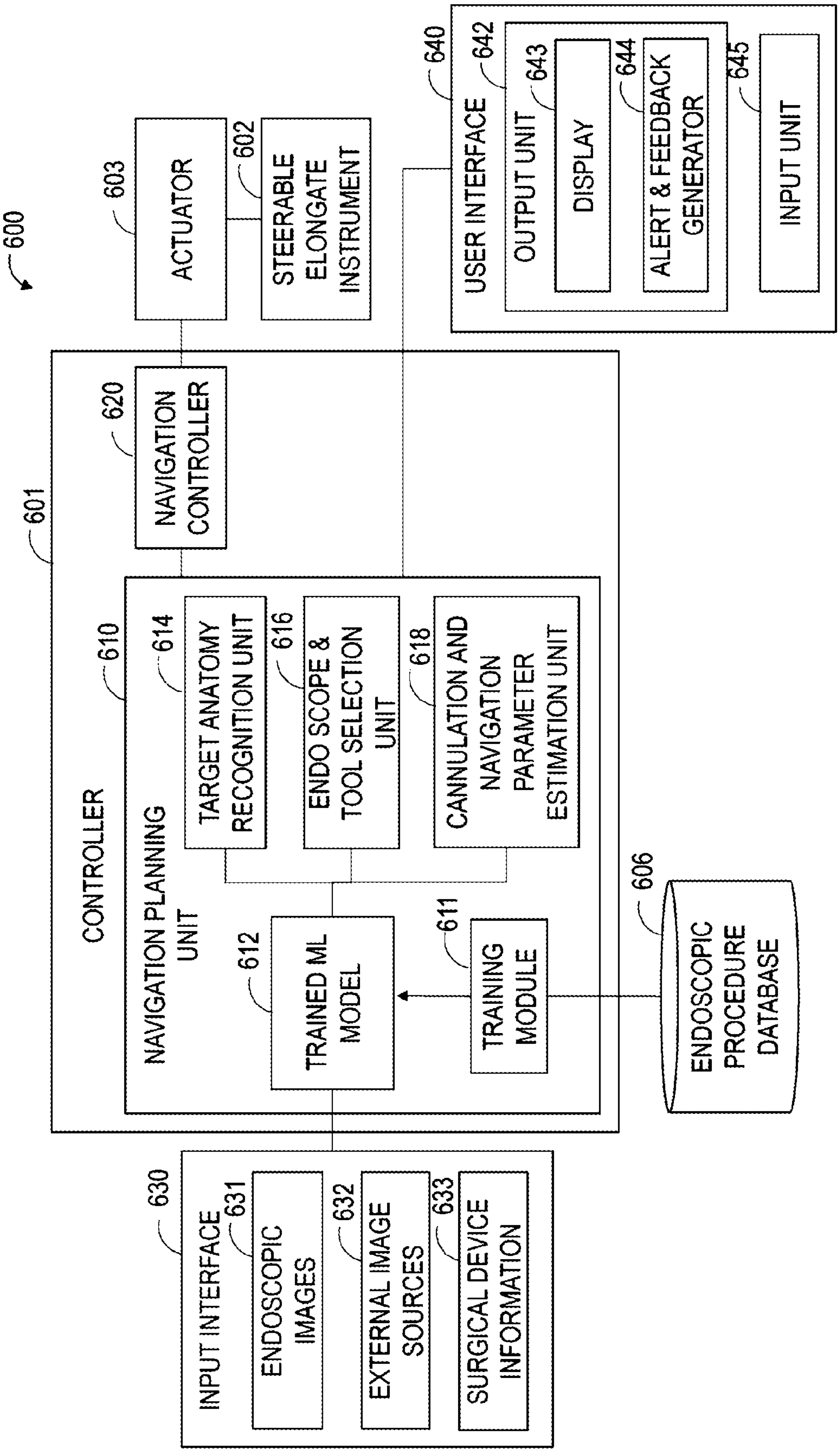
FIG. 14 illustrates an example of an image-guided navigation system for planning an endoscopic procedure in a surgically altered GI anatomy.

FIG. 14 is a block diagram illustrating by way of example and not limitation an image-guided navigation system 600 for planning an endoscopic procedure in a surgically altered GI anatomy. The system 600 can be a part of the control unit 16 in FIG. 8, or the controller 408 in FIG. 12 along with other devices or functional units such as the endoscopic procedure data generator 450 and the treatment plan generator 460.

The image-guided navigation system 600 may include a controller 601, an input interface 630, and a user interface 640. The system 600 may additionally include optional one or more actuators 603 coupled to a steerable elongate instrument 602 to adjust its position, direction, or force applied thereto during a robotically assisted endoscopic procedure. The controller 601 may include circuit sets comprising one or more other circuits or sub-circuits, including a navigation planning unit 610 and a navigation controller 620. These circuits may, alone or in combination, perform the functions, methods, or techniques described herein. In an example, the controller 601 and the circuits sets therein may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The navigation planning unit 610 may generate an endoscope navigation plan with respect to an anatomical target of interest (e.g., duodenal papilla) using information from one or more input data sources. By way of example and not limitation, the input interface 630 may include one or more of endoscopic images 631 of the target anatomy, external image sources 632, and surgical device information 633, as illustrated in FIG. 14. The endoscopic images 631 may include real-time perioperative images of the surgically altered anatomy taken by imaging sensors associated with the endoscope during an endoscopy procedure, such as perioperative optical endoscopic images by an camera or optical imaging sensor and/or perioperative EUS images produced by an ultrasound transducer during an echoendoscopy procedure. The endoscopic images 631 may additionally include endoscope images of duodenal papilla and its surrounding environment captured by the imaging sensor on the endoscope during an endoscopic procedure, such as the DPOC procedure or an ERCP procedure as described above in reference to FIGS. 11A-11B and FIG. 12, respectively. The external image sources 632 may include preoperative or perioperative images of surgically altered anatomy and its surrounding environment from external imaging devices (other than the endoscope), which may include, for example, X-ray or fluoroscopy images, electrical potential map or an electrical impedance map, CT images, MRI images such as images obtained from Magnetic resonance cholangiopancreatography (MRCP) procedures, or acoustic images such as endoscopic ultrasonography (EUS) images, among others. The surgical device information 633 may include specification data, including dimension, shape, and structures of the endoscope used in an ERCP procedure or other steerable instruments such as a cannular, a catheter, or a guidewire. Such device specification information may be used to determine cannulation or navigation parameter values such as the angle and/or the force applied to the device. In addition to the images from various sources or of different modalities and the surgical device information, in some examples, the input interface 630 may receive sensor signals acquired by sensors coupled to the endoscope, or otherwise associated with the patient. Examples of the sensor signals may include position, direction, or proximity of a distal portion of the endoscope relative to duodenal papilla. In some examples, the input interface 630 may receive physician/patient information, such as the operating physician's habits or preference of using the steerable elongate instrument 602, such as a preferred approach for cannulation and endoscope navigation, or past procedures of the similar type to the present procedure performed by the physician and the corresponding procedure outcome (e.g., success/failure, procedure time, prognosis and complications). The physician/patient information 635 may include patient information, such as endoscopic images or other sensor information, patient medical history, etc.

The navigation planning unit 610 may include one or more of a target anatomy recognition unit 614, an endoscope or tool selection unit 616, and a cannulation and navigation parameter estimation unit 618. The target anatomy recognition unit 614 can automatically recognize the anatomical target of interest such as from a received image (e.g., endoscopic images 631 and/or external image sources 632). In an example, the target anatomy recognition unit 614 can analyze preoperative images to recognize an anatomical structure (e.g., duodenal papilla), and determine one or more positional or geometric parameters of the anatomical structure. For example, the target anatomy recognition unit 614 may recognize papilla from the input image, and determine the position, shape, and orientation (angle) of the papillary orifice with respect to the duodenum 308 and the ductal system (e.g., the common bile duct 312). In an example, the target anatomy recognition unit 614 may recognize the surgically altered GI anatomy from the preoperative and/or perioperative images, and estimate the length and route of a GI tract portion for passing the endoscope, such as from mouth to papilla through at least a portion of the surgically altered GI anatomy. In another example, the target anatomy recognition unit 614 may estimate the angle between a portion of the GI route (e.g., duodenum portion proximal to the papillary orifice) and a target duct of the pancreaticobiliary anatomy (e.g., the common bile duct 312 or the pancreatic duct 316) into which the selected endoscope is to reach. Such positional or geometric parameters may be used for selecting proper endoscope or other surgical tools and planning the endoscopic procedure for the patient.

The endoscope or tool selection unit 616 can determine an endoscope or tool recommendation for use in an endoscopic procedure based at least on the input image (e.g., endoscopic images 631 and/or external image sources 632) and the recognized anatomical target and the associated positional or geometric parameters. The endoscope or tool recommendation may include a recommended tool size, type, shape, or length. In an example, the endoscope or tool selection unit 616 can generate a recommendation of an endoscopes of a specific type and length suitable for passing through the surgically altered GI anatomy into an pancreaticobiliary anatomy of the patient. For example, based on the estimated length of the GI route (e.g., from mouth to papilla through the surgically altered GI anatomy) by the target anatomy recognition unit 614, an endoscope longer than the estimated length of the GI route but within a predetermined margin can be recommended for use in the endoscopic procedure. In another example, a forward-viewing endoscope or a side-viewing endoscope can be selected based on the estimated angle between the GI route and a target duct by the target anatomy recognition unit 614. Side-viewing duodenoscopes have the advantage of looking at the major duodenal papilla en-face. However, in some patients it is impossible or difficult to reach the papillary area due to the length of the afferent loop. The forward-viewing endoscope has a long-working length and permits the operator to enter the afferent loop easily and safely because of the ability to see the lumen en-face. Forward-viewing endoscope for ERCP have also been used surgically altered anatomy such as in Billroth II gastrectomy patients to improve exposure of the papilla. In an example, a side-viewing scope is recommended if the estimated angle between the GI route and a target duct exceeds a threshold angle or falls within a first range of angles, and a forward-viewing scope is recommended if the estimated angle between the GI route and a target duct is below the threshold angle or falls within a second range of angles different than the first range. In some examples, the target anatomy recognition unit 614 may estimate the length and route of a GI tract portion for passing the endoscope further using a user input designating a starting point and an end point of the altered GI tract for passing the selected endoscope. The endoscope or tool selection unit 616 can generate the recommendation of the endoscope type and length based on the estimated length of GI route. In addition or alternative to recommendation of endoscope type and length, in some examples, the endoscope or tool selection unit 616 can generate a recommendation of a surgical tool associated with the selected endoscope, such as tools for tissue resection, tissue biopsy, calculi object extraction, drainage, stricture management, among others, based on the input image and the recognized anatomical target and the associated positional or geometric parameters.

The cannulation and navigation parameter estimation unit 618 can automatically estimate values for one or more cannulation or navigation parameters, which may include, for example: a position of the distal portion (e.g., the functional section 30 of the endoscope 14 as shown in FIG. 8) of an endoscope or other steerable elongate instrument relative to an anatomical target of interest, such as a distance from the endoscope distal portion to duodenal papilla; a heading direction of the distal portion of the steerable elongate instrument relative to the anatomical target; an insertion angle of a cannula or a surgical element used in cannulation; a protrusion amount of a cannula or a surgical element; a speed or a force applied to the endoscope distal portion or a surgical element; a rotational direction or a cutting area of a surgical element; a navigation path for navigating the endoscope (or other steerable elongate instrument) to the anatomical target while avoiding injury or damage to internal organs or tissue (e.g., pancreas or vessels), among others.

One or more of the target anatomy recognition unit 614, the scope and tool selection unit 616, or the cannulation and navigation parameter estimation unit 618 can each use one or more trained machine-learning (ML) models 612 to perform their respective tasks as stated above. The ML model(s) can have a neural network structure comprising an input layer, one or more hidden layers, and an output layer. The input interface 630 may deliver one or more sources of input data, or features generated therefrom, into the input layer of the ML model(s) 612 which propagates the input data or data features through one or more hidden layers to the output layer. The ML model(s) 612 can provide the system 600 with the ability to perform tasks, without explicitly being programmed, by making inferences based on patterns found in the analysis of data. The ML model(s) 612 explores the study and construction of algorithms (e.g., ML algorithms) that may learn from existing data and make predictions about new data. Such algorithms operate by building the ML model(s) 612 from training data in order to make data-driven predictions or decisions expressed as outputs or assessments.

The ML model(s) 612 may be trained using supervised learning or unsupervised learning. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Unsupervised learning is the training of an ML algorithm using information that is neither classified nor labeled, and allowing the algorithm to act on that information without guidance. Unsupervised learning is useful in exploratory analysis because it can automatically identify structure in data.

Common tasks for supervised learning are classification problems and regression problems. Classification problems, also referred to as categorization problems, aim at classifying items into one of several category values. Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types or different model configurations.

Some common tasks for unsupervised learning include clustering, representation learning, and density estimation. Some examples of commonly used unsupervised learning algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

As illustrated in FIG. 14, the ML model(s) 612 may be trained using a training module 611, which can be included in the navigation planning unit 610 as shown in FIG. 14. Alternatively, the training module 611 can be implemented in a separate unit. To train the ML model, a training dataset can be constructed using one or more of the input interface 630, and past endoscopic procedure data such as selected and retrieved from the endoscopic procedure database 606. In an example, the training data can be screened such that only data of procedures performed by certain physicians (such as those with substantially similar experience levels to the operating physician), and/or data of procedures on certain patients with special requirement (such as those with substantially similar anatomy or patient medical information to the present patient) are included in the training dataset. In an example, the training data can be screened based on a success rate of the procedure, including times of attempts before a successful cannulation or navigation, such that only data of procedures with a desirable success rate achieved within a specified number of attempts are included in the training dataset. In another example, the training data can be screened based on complication associated with the patients. In some examples, particularly in case of a small training dataset (such as due to data screening), the ML model can be trained to generate a treatment plan by extrapolating, interpolating, or bootstrapping the training data, thereby creating a treatment plan specifically tailored to the specific patient and physician. The training of the ML model may be performed continuously or periodically, or in near real time as additional procedure data are made available. The training involves algorithmically adjusting one or more ML model parameters, until the ML model being trained satisfies a specified training convergence criterion.

In some examples, a plurality of ML models can be separately trained, validated, and used (in an inference phase) in different applications, such as estimating different parameters of the devices used in an endoscopic procedure or planning of such a procedure. For example, a first ML model (or a first set of ML models) may be trained to establish a correspondence between (i) endoscopic images and/or other external images of altered GI anatomy and the anatomical target from past endoscopic procedures (optionally along with other information) and (ii) characteristics of the target anatomy such as location, size, shape, orientation, and pathophysiological properties of the anatomical target, and positional or geometric parameters associated with the anatomical target. The trained ML model(s) can be used by the target anatomy recognition unit 614 in an inference phase to identify, from an input image (or a sequence of images or a live video) of an anatomical target (optionally along with other information), characteristics of the anatomical target and positional or geometric parameters associated therewith.

In an example, a second ML model (or a second set of ML models) may be trained to establish a correspondence between (i) endoscopic images and/or other external images of altered GI anatomy and the anatomical target from past endoscopic procedures (optionally along with other information) and (ii) endoscope and tools used in those past procedures, and the tool characteristics including their types, sizes, and operational parameters. The trained second ML model(s) can be used by the scope and tool selection unit 616 in an inference phase to automatically determine, from an input image (or a sequence of images or a live video), an endoscope or tool recommendation of a particular type and size and operational parameters for manipulating the tool during the procedure.

In another example, a third ML model (or a third set of ML models) may be trained to establish a correspondence between (i) endoscopic images and/or other external images of altered GI anatomy and the anatomical target from past endoscopic procedures (optionally along with other information) and (ii) navigation and treatment parameters in those past procedures, including direction, angle, speed, force, and amount of intrusion for navigating and placing endoscopes, catheters, or other steerable elongate instrument over which a tissue acquisition device is deployed, or estimated success rate and procedure time, among other parameters. The trained second ML model(s) can be used by the cannulation and navigation parameter estimation unit 618 in an inference phase to automatically determine, from an input image (or a sequence of images or a live video) of patient anatomy including the anatomical target (optionally along with other information), proper navigation parameters that may be used as a procedure guidance.

The navigation controller 620 can generate a control signal to the one or more actuators 603, such as a motor actuating a robot arm. The one or more actuators 603 can be coupled to the steerable elongate instrument 602, such as a proximal portion thereof. Examples of the steerable endoluminal instrument 602 may include diagnostic or therapeutic endoscopes, cannulas, catheters, guidewires, or guide sheaths, among others. In response to the control signal, the one or more actuators 603 can robotically adjust position or navigation of the steerable elongate instrument 602 in the target anatomy in accordance with the one or more cannulation or navigation parameters estimated by the cannulation and navigation parameter estimation unit 618. As some of the canulation or navigation parameters (e.g., positions, angle, direction, navigation path) associated with a cannula or GW are determined based on images (e.g., endoscopic images or other images) generated an imaging system, such canulation or navigation parameters are with reference to the coordinates of the imaging system. To facilitate robotic control of the cannula or GW in accordance with the canulation or navigation parameters, in some examples the coordinates of the robotic system may be registered with the coordinates of the imaging system, such that an anatomical position in the coordinates of the imaging system can be mapped to a corresponding position in the coordinates of the robotic system. Such registration may be performed, for example, by using distinct landmarks whose positions are known in respective coordinate systems. The registration may be intensity- or feature-based, and can be represented by transformation model (a linear or a non-linear model) that maps the coordinates of imaging system to the coordinates of the robotic system.

In an example, the cannulation and navigation parameter estimation unit 618 can determine a force applied to a cannula or GW (an example of the steerable elongate instrument 602) based on a distance from the distal tip of the cannula/GW to duodenal papilla. Such distance can be determined using sensor signals 634, such as via a proximity sensor at the tip of the cannula/GW. In another example, the distance can be measured by a displacement sensor, disposed on the actuator 603 or a robot arm coupling to the cannula/GW, that measures a length of insertion into duodenal papilla. Additionally or alternatively, the distance can be estimated from the endoscopic images 631. With the information about the distance between the distal tip of the cannula/GW to duodenal papilla, the cannulation and navigation parameter estimation unit 618 can determine a lower force applied to a cannula/GW as the distal tip of the cannula/GW gets closer to duodenal papilla. In an example, the applied force can be inversely proportional to said distance. After the distal tip of the cannula/GW being inserted into and passing through duodenal papilla, the navigation parameter estimation unit 616 can determine a lower level or range of force than the force level or range before the insertion. The navigation controller 620 can then control the actuator 603 (or the robot arm) to apply the distance-dependent force as determined above to the cannula/GW. Dynamically adjusting the force based on the distance to the critical anatomy (e.g., duodenal papilla, common bile duct, and pancreas) as described herein can avoid or reduce damage to pancreatic parenchyma caused by cannula/GW. Robotic assistance can increase the precision of cannula/GW positioning and advancement at or near the critical anatomy, and further reduce the risk of tissue damage due to improper cannulation.

In an example, the cannulation and navigation parameter estimation unit 618 can determine an insertion angle of a cannula or GW (an example of the steerable elongate instrument 602) and/or a force applied to the cannula or GW based at least on surgical device information 633. Such device information may include specifications of an endotherapeutic device such as inner and outer diameters, tip shape, tip load and/or stiffness, torquability (an ability of rotating element to overcome tuning resistance), bending angle, wire support (a measure or wire's resistance to a bending force), among others. An ML model may be trained to establish between the specifications of a cannula or GW and a proper insertion angle or force applied thereto. The cannulation and navigation parameter estimation unit 618 can feed the specifications of the cannula or GW presently used in the procedure to the trained ML model to estimate a proper insertion angle and/or force applied to the cannula or GW.

In an example, after the cannula/GW is inserted into duodenal papilla, the cannulation and navigation parameter estimation unit 618 can determine a direction, or a navigation path, for advancing the cannula/GW within the common bile duct or other portions of pancreaticobiliary system. Such direction or navigation path can be determined based on endoscopic images 631 and/or external image sources 632, such as images of the common bile duct or other portions of pancreaticobiliary system. The images may include one or more of endoscopic images obtained prior to or during an ERCP procedure, MRI images obtained prior to or during an MRCP procedure, among others. The cannulation and navigation parameter estimation unit 618 can determine the direction using a trained ML model 612. In an example, the ML model 612 can be trained using reinforcement learning. Reinforcement learning is a machine learning approach for creating behavior policies (e.g., the cannula/GW's heading direction) under certain states in an environment in order to maximize cumulative rewards associated with the behavior policies. In contrast to supervised learning which uses labelled input/output pairs to train the model, reinforcement learning maintains a balance between exploration of uncharted territory (e.g., different heading directions or paths to take within the common bile duct or the pancreaticobiliary system) and exploitation of current knowledge during the model training process. For example, reinforcement learning allows the model being trained to actively gather experience in situations where it performs poorly without needing external interventions, and can directly optimize behavior performance through the reward function. In the above example of ML-based determination of a heading direction or navigation path for the cannula/GW, the reinforcement learning can be advantageous especially with the lack of labelled training data such as from past procedures performed by a plurality of physicians on a plurality of patients. The navigation controller 620 can control the actuator 603 (or the robot arm) to orient the distal portion of the cannula/GW in accordance with the determined direction and navigate through the pancreaticobiliary system in accordance with the determined navigation path.

In some examples, the cannulation and navigation parameter estimation unit 618 can determine an insertion angle of a cannula/GW (an example of the steerable elongate instrument 602) based on past endoscopic procedure data stored in the endoscopic procedure database 606. The stored procedure data may include, for each procedure, endoscopic images or videos showing patient anatomy, cannulation and endoscope navigation paths, progress of cannulation and navigation, the physician's information, among other information. In an example, the stored procedure data may include, for each procedure, one or more cannulation or navigation parameters that are recorded during the procedure, or obtained by offline analysis the endoscopic images or videos. The stored procedure data may also include indications of physicians' habits or preferred procedure approaches. In various embodiments, at least a portion of the stored procedure data is used as a training set for training a ML model that predicts the cannulation and navigation parameter(s) of a procedure to be performed at a later time. In an example, the training data can be screened such that only data of procedures performed by certain physicians (such as those with substantially similar experience levels to the operating physician), and/or data of procedures on certain patients with special requirement (such as those with substantially similar anatomy or patient medical information to the present patient) are included in the training dataset. Additionally, in some examples, the surgical device information 633, such as endoscopes used in ERCP procedures, may be included in the ML model training process. The cannulation and navigation parameter estimation unit 618 can determine, for example, the insertion angle of a cannula/GW using the trained ML model. The navigation controller 620 can then control the actuator 603 (or the robot arm) to position the distal portion of the cannula/GW and insert into the duodenal papilla in accordance with the determined insertion angle.

In some examples, an ML model may be trained using past imaging data and procedure data stored in the endoscopic procedure database 606 to produce multiple reference control patterns, such as multiple reference heading directions or reference navigation paths, multiple insertion angles, or multiple force levels or force ranges to apply to the steerable elongate instrument 602 (e.g., a cannula/GW). The multiple reference control patterns can be sorted, or otherwise categorized into groups, based on one or more of success rate, patient outcome and prognosis, procedure time, among other qualifications. The cannulation and navigation parameter estimation unit 618 can, based on the imaging data of the current patient, select from the reference control patterns at least one that corresponds to, for example, the highest success rate or a specified success rate (e.g., having a success rate exceeding 90%). The navigation controller 620 can then control the actuator 603 (or the robot arm) to control the positioning and motion of the cannula/GW in accordance with the selected reference control pattern. In addition, based on the feedback received from the live procedure, the cannulation and navigation parameter estimation unit 618 can switch from one reference control pattern to a different reference control pattern.

According to some examples, two or more different ML models can be separately trained, validated, and used in different applications including, for example, target anatomy recognition, cannulation or navigation parameter estimation, automatic endoscope positioning and navigation, automatic insertion of cannula or a guidewire (hereinafter a "cannula/GW") in the target anatomy, among others. For example, a ERCP procedure may involve multiple steps including passing an endoscope down to the duodenum and recognizing duodenal papilla, inserting a cannula/GW to the papilla, and adjusting direction or force of the cannula/GW to avoid excess pressure to the pancreas. Different ML models may be trained and used in respective steps of the ERCP procedure. In an example, to identify the location of papilla and locating the endoscope to be in front of papilla, a reinforcement learning model may be trained using endoscopic images 631 of papilla and endoscope control log data 636 to determine precise location of the endoscope relative to the papilla. The cannulation and navigation parameter estimation unit 618 can use said reinforcement learning model to determine if the endoscope is in front of papilla. The navigation controller 620 can generate a control signal to guide endoscope positioning if it is determined that the endoscope is not in front of papilla.

In another example, separated ML models may be trained to perform different functions, such as a first ML model being trained to recognize a region of interest, and a second ML model being trained to determine optimal cannulations parameters associated with the recognized region of interest. For example, to control the endoscope such that the papilla is captured in the center of the endoscope image and to guide insertion of a cannula/GW to the center of papilla from an optimal direction or position, a first supervised learning model may be trained to recognize duodenal papilla with certain spatial or geometrical characteristics thereof, such as the center of the papilla for endoscopic access or cannulation. Additionally, a second reinforcement learning model may be trained to determine an optimal direction to move the endoscope to capture the center of papilla. The first supervised learning model and the second reinforcement learning model can be separately trained each using one or more of endoscopic images 631 of papilla, external image sources 632 such as MRI image of bile duct, and endoscope control log data 636. The target anatomy recognition unit 614 can use the trained supervised learning model to localize the center of duodenal papilla.

Figure 15:
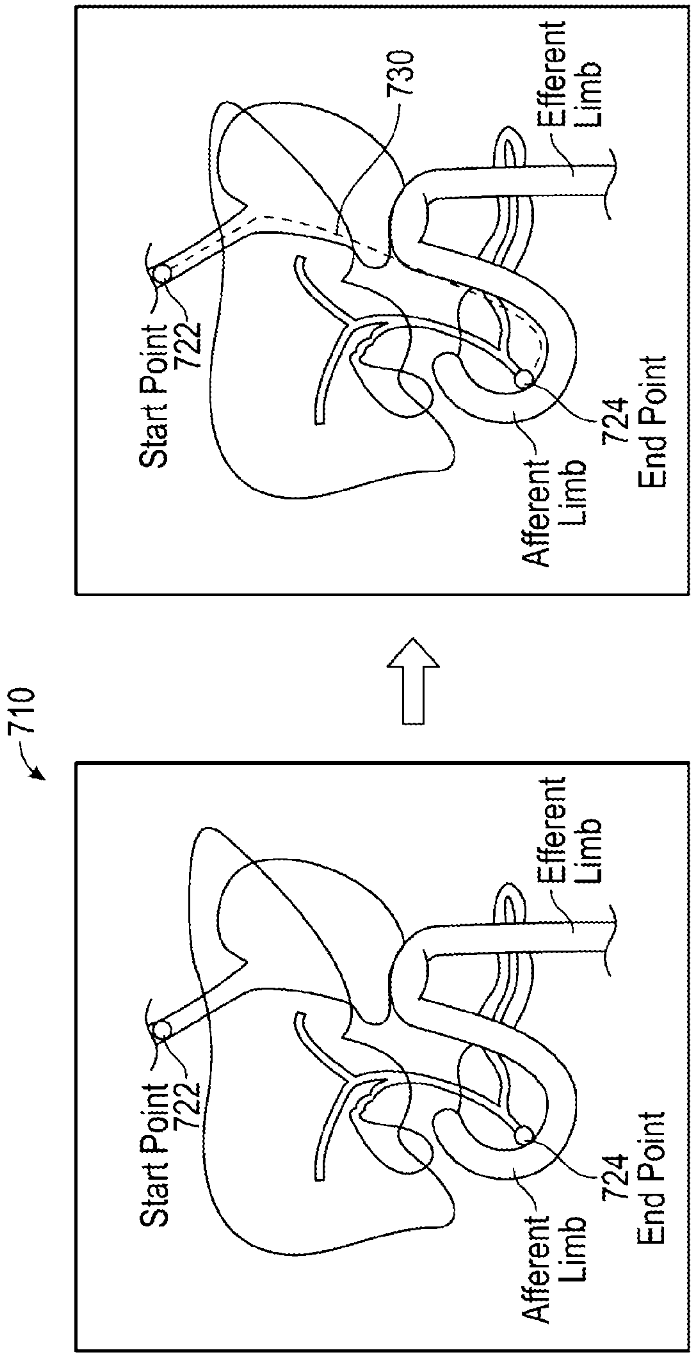
FIG. 15 illustrates an example of identifying a navigation route for passing an endoscope in a portion of the GI tract with surgically altered anatomy.

FIG. 15 illustrates an example of identifying a route for passing the endoscope along a portion of the GI tract with surgically altered anatomy. By way of example, a GI anatomy post Billroth II gastrectomy as illustrated in FIG. 13A in shown. The navigation route identification technique as described herein can be similarly applied to other surgically or non-surgically altered gastric anatomy. From an preoperative image 710, anatomical structures of portions of the GI tract (e.g., stomach and afferent limb and efferent limb of the duodenum) can be identified such as using the target anatomy recognition unit 614. The preoperative image 710, along with identification of the anatomical structures, can be displayed on a display 643 of an output unit 642 of a user interface 640. The output unit 642 can include an alert and feedback generator 642 to generate an alert or feedback about endoscope navigation to the operator. An operator (e.g., an endoscopist) may use the input unit 645 of the user interface 640 to designate a starting point 722 and an end point 724 of the altered GI anatomy for passing an endoscope. By way of example and as shown in FIG. 15, the starting point 722 is in proximity to an upper portion of esophagus, and the end point 724 is proximal to duodenum papilla, the position of which can be identified by target anatomy recognition unit 614. Using the preoperative image 710 and the user designated starting point 722 and the end point 724, the target anatomy recognition unit 614 can estimate the length of a GI route 730 between the starting point 722 and the end point 724. The GI route is a portion of the GI tract for passing the endoscope. The information of the GI route 730 and estimated length thereof can be presented to the user on the user interface. Based on the estimated length of GI route 730, the endoscope or tool selection unit 616 can generate a recommendation of an endoscope longer than the estimated length of a GI route 730 but within a predetermined margin.

Figure 16A:
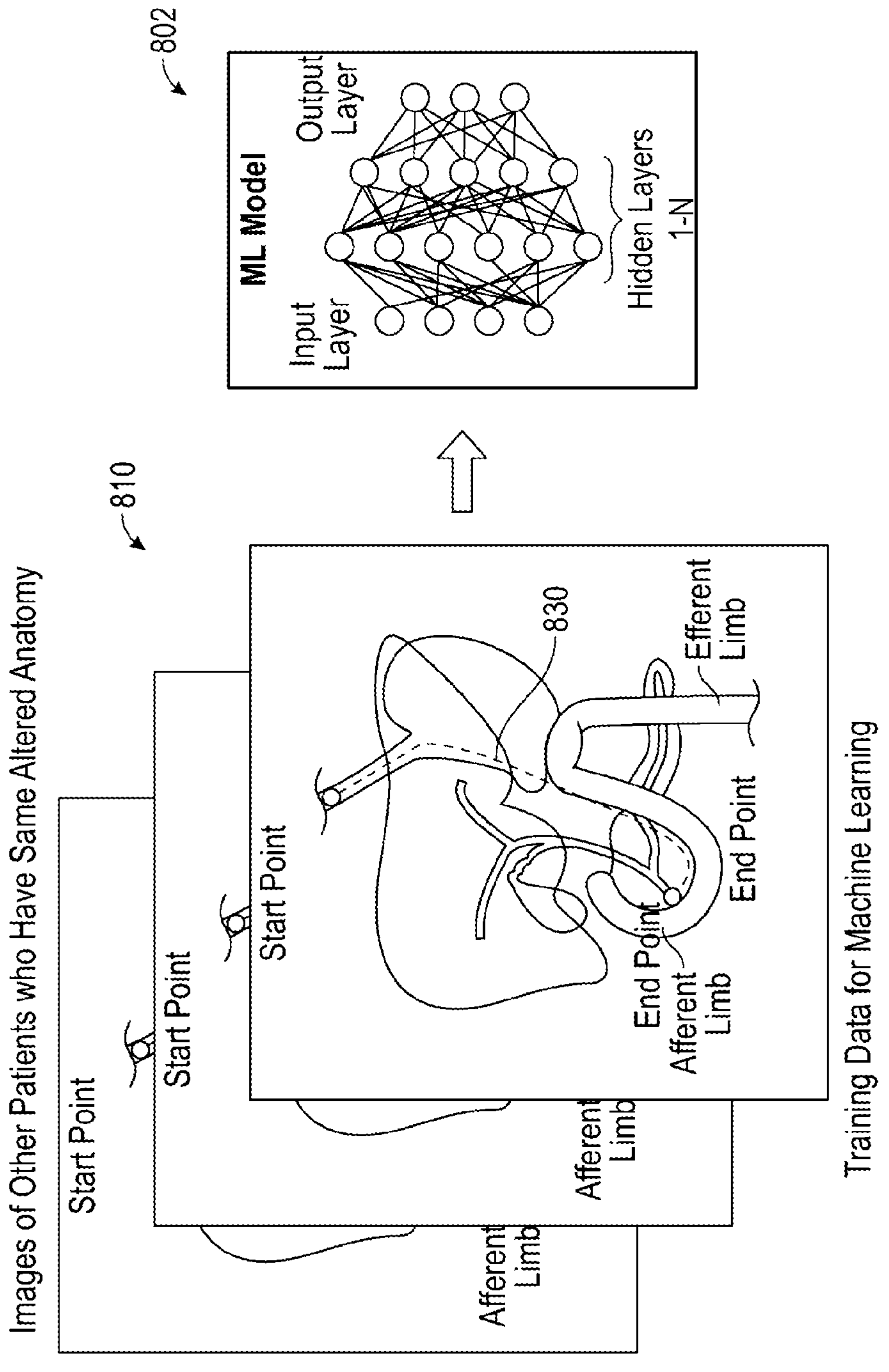
FIGS. 16A-16B illustrate an example of training a machine learning (ML) model, and using the trained ML model to generate a endoscopy plan.
Figure 16B:
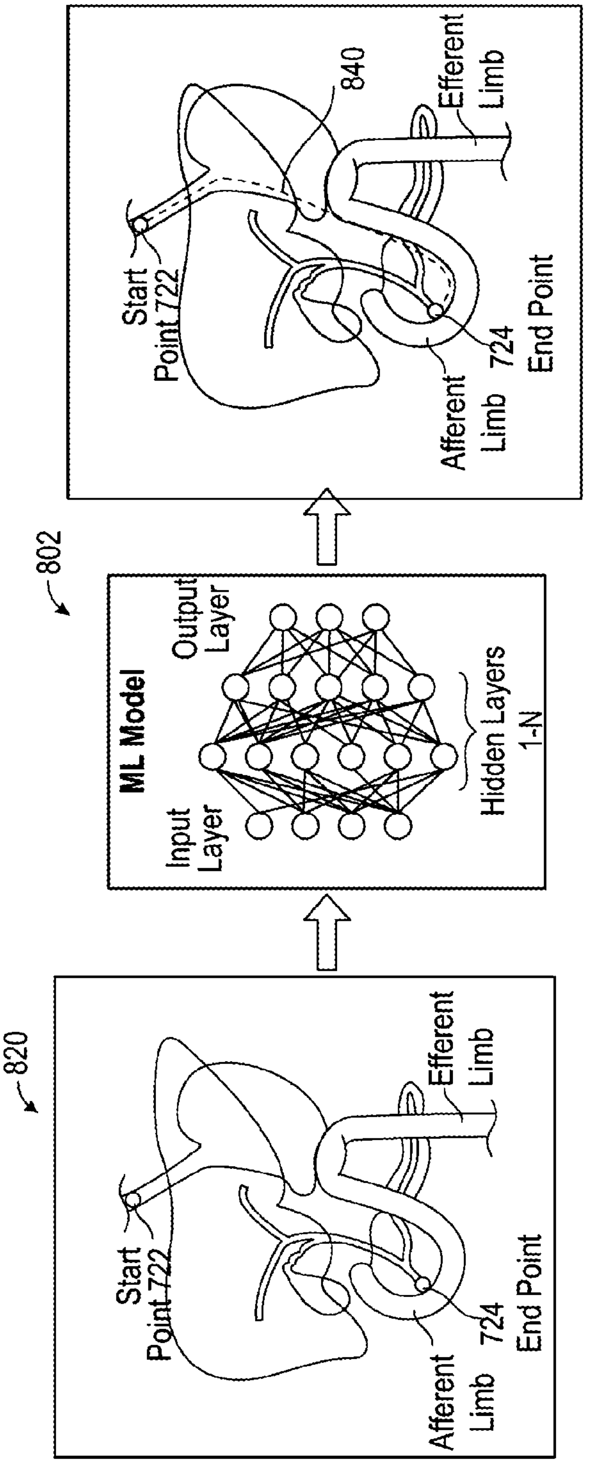

FIGS. 16A-16B are diagrams illustrating an example of training a machine learning (ML) model, and using the trained ML model to generate a endoscopy plan, including an estimate the GI route in the surgically altered GI anatomy and providing recommendations of an endoscope of specific length and type for use in the endoscopic procedure. FIG. 16A illustrates an ML model training (or learning) phase during which an ML model 802 may be trained using training data comprising a plurality of preoperative images 810 of altered GI anatomy and the anatomical target. The preoperative images can be taken from past endoscopic procedures in patients with similar altered GI anatomy as the test patient. The training data may also include annotated procedure data including information about identified anatomical structures (e.g., papilla) and the GI routes 830 for passing the endoscope for the respective preoperative images 810. In some examples, the training data may also include endoscopes and surgical tools (e.g., type, size, length) being used in the endoscopic procedures in the surgically altered anatomy. In some examples, the training data may further include operational data associated with the use of such endoscopes or tools in the past endoscopic procedures. The training data may also include procedure outcome, such as success/failure assessment of the procedure, total procedure time, procedure difficulty and skills requirement, etc. The ML model 802 can be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations. The training of the ML model may be performed continuously or periodically, or in near real time as additional procedure data are made available. The training process involves algorithmically adjusting one or more ML model parameters, until the ML model being trained satisfies a specified training convergence criterion. The trained ML model 802 establishes a correspondence between the images of the altered GI anatomy and the anatomical target from past endoscopic procedures and the positional or geometric parameters associated with an anatomical target, such as a GI route (e.g., between user designated starting point and end point as shown in FIG. 15) and estimated length of the GI route. The trained ML model 802 (or alternatively a separated ML model being trained) can establishes a correspondence between the images of the altered GI anatomy and the anatomical target and endoscope and tools used in those past procedures, and the tool characteristics including their types, sizes, and operational parameters.

FIG. 16B illustrates an inference phase during which a preoperative image 820 of the test patient is applied to the trained ML model 802 to automatically identify anatomical structures (e.g., papilla), determine a GI route 840, and estimate the length of a GI route 840 such as between starting and end points designated by the user. In some examples, the trained ML model 802 can automatically generate a recommendation of an endoscope longer than the estimated length of a GI route 840 but within a predetermined margin. The GI route 840 and the recommendation of the endoscope can be communicated to a user to assist in procedure planning. Additionally or alternatively, the GI route 840 and the recommended endoscope information may be provided to a robotic endoscopy system to facilitate a robot-assisted endoscopic procedure.

Figure 17:
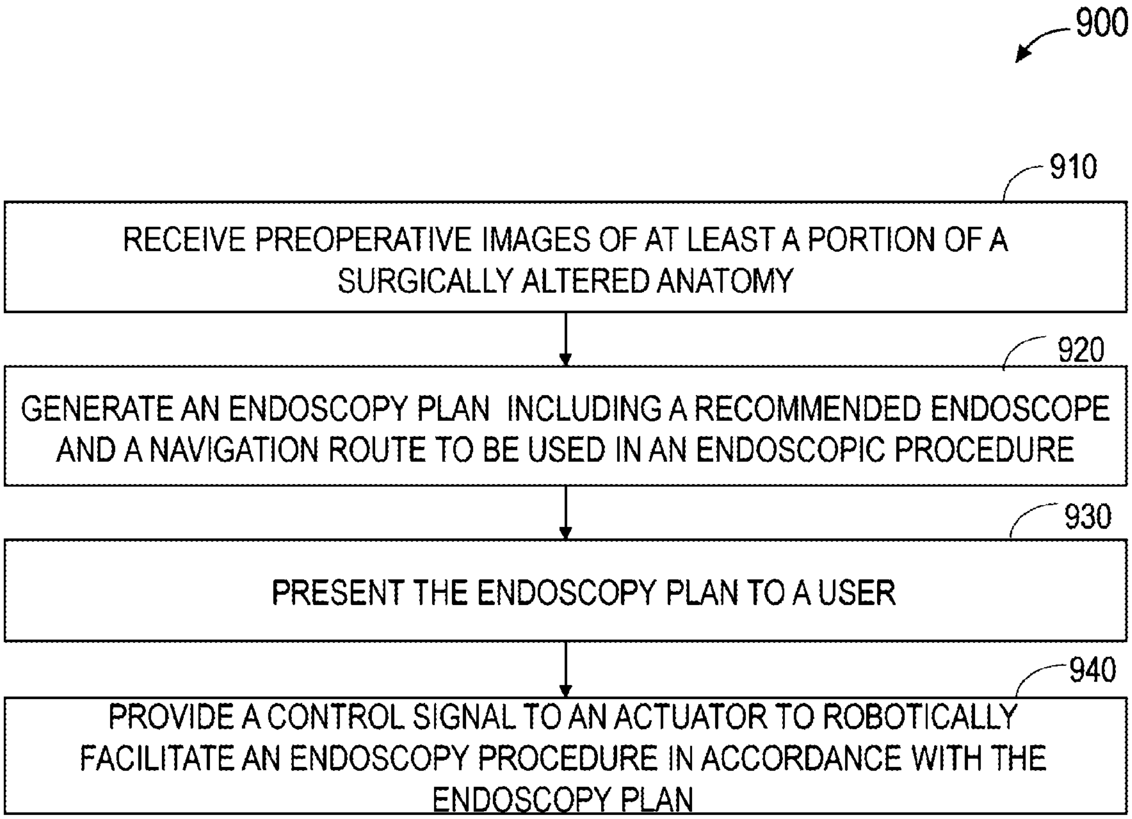
FIG. 17 is a flow chart illustrating an example method for planning an endoscopic procedure in a surgically altered anatomy.

FIG. 17 is a flow chart illustrating an example method 900 for planning an endoscopic procedure in a surgically altered anatomy. The method 900 may be implemented in and executed by the image-guided navigation system 600. Although the processes of the method 900 are drawn in one flow chart, they are not required to be performed in a particular order. In various examples, some of the processes can be performed in a different order than that illustrated herein.

At 910, preoperative images of at least a portion of a surgically altered GI anatomy through which an endoscope is to pass can be received, such as via the input interface 630 of the system 600. In some examples, preoperative images of a non-surgically altered GI anatomy may be received. The receive preoperative images may include, for example, a fluoroscopic image, a CT scan image, an MRI scan image, an electrical potential map or an electrical impedance map, an MRCP image, or an EUS image. In some examples, endoscopic images, including perioperative optical endoscopic images and/or perioperative EUS images of the surgically altered anatomy taken during an endoscopy procedure may also be received at 910. In some examples, surgical device information including, for example, dimension, shape, and structures of the endoscope used in an ERCP procedure or other steerable instruments such as a cannular, a catheter, or a guidewire, may be received at 910 interface.

At 920, an endoscopy plan can be generated using the received preoperative images. The endoscopy plan may include an endoscope or tool recommendation for use in an endoscopic procedure, and a navigation route for passing the endoscope through the surgically altered anatomy during the endoscopic procedure. In an example, the navigation plan can include a navigation route along at least a portion of the GI tract toward a target portion in preoperative images of the non-surgically altered anatomy. To facilitate automatic selection of the endoscope or tool and determination of navigation route, an anatomical target of interest (e.g., duodenal papilla) can be automatically recognized from the received images, and one or more positional or geometric parameters associated of the anatomical structure can be determined. In an example, the surgically altered GI anatomy may be recognized from the received images, and the length and route of a GI tract portion for passing the endoscope (e.g., from mouth to papilla, through at least a portion of the surgically altered GI anatomy) can be estimated using the received images. In another example, the angle between a portion of the GI route (e.g., duodenum portion proximal to the papillary orifice) and a target duct of the pancreaticobiliary anatomy (e.g., the common bile duct 312 or the pancreatic duct 316) can be estimated using the received images. Such positional or geometric parameters may be used for selecting proper endoscope or other surgical tools and planning the endoscopic procedure for the patient.

The endoscope or tool recommendation may include a recommended tool size, type, shape, or length suitable for the endoscopic procedure, such as suitable for passing through the surgically altered GI anatomy into an pancreaticobiliary anatomy of the patient. In an example, based on the estimated length of the GI route (e.g., from mouth to papilla through the surgically altered GI anatomy), an endoscope longer than the estimated length of the GI route but within a predetermined margin can be recommended for use in the endoscopic procedure. In another example, a forward-viewing endoscope or a side-viewing endoscope can be selected based on the estimated angle between the GI route and a target duct. In some examples, the length and route of a GI tract portion for passing the endoscope can be estimated further based on a user input designating a starting point and an end point of the altered GI tract for passing the selected endoscope, as described above with reference to FIG. 15. In addition or alternative to recommendation of endoscope type and length, a recommendation of a surgical tool associated with the selected endoscope, such as tools for tissue resection, tissue biopsy, calculi object extraction, drainage, stricture management, among others, can be generated based on the received image and the recognized anatomical target and the associated positional or geometric parameters The endoscopy plan may include estimated values for one or more cannulation or navigation parameters, which may include, for example: a position of the distal portion of an endoscope or other steerable elongate instrument relative to an anatomical target of interest, such as a distance from the endoscope distal portion to duodenal papilla; a heading direction of the distal portion of the steerable elongate instrument relative to the anatomical target; an insertion angle of a cannula or a surgical element used in cannulation; a protrusion amount of a cannula or a surgical element; a speed or a force applied to the endoscope distal portion or a surgical element; a rotational direction or a cutting area of a surgical element; a navigation route for navigating the endoscope (or other steerable elongate instrument) to the anatomical target while avoiding injury or damage to internal organs or tissue (e.g., pancreas or vessels), among others.

In various examples as described above with reference to FIG. 14, at least a part of the endoscopy plan (e.g., target anatomy recognition, the endoscope and tool selection, and cannulation and navigation parameter estimation) can be determined using one or more trained machine-learning (ML) models. The ML models can be respectively trained using supervised learning or unsupervised learning on training data including image data from past endoscopic procedures on a plurality of patients.

At 930, the image of the anatomical target and the endoscopy plan may be presented to a user, such as being displayed on a display of a user interface. In some examples, a graphical representation of the navigation of an endoscope based on the navigation parameters and/or a graphical representation of the operation of a tissue acquisition tool based on the tool operational parameters can also be displayed on the user interface.

At 940, a control signal may be provided to an actuator to robotically facilitate operation of the endoscope or other tools associated therewith to treat the anatomical target in accordance with the endoscopy plan determined at step 920. The actuator can be a motor actuating a robot arm operably coupled to the endoscope. The endoscope may include a surgical tool robotically operable via the actuator. In response to the control signal, the actuator can robotically adjust position, posture, direction, and navigation route of the endoscope and the surgical tool included therein to perform endoscopic procedure in accordance with the navigation parameters and/or the tool operational parameters generated at 920.

Figure 18:
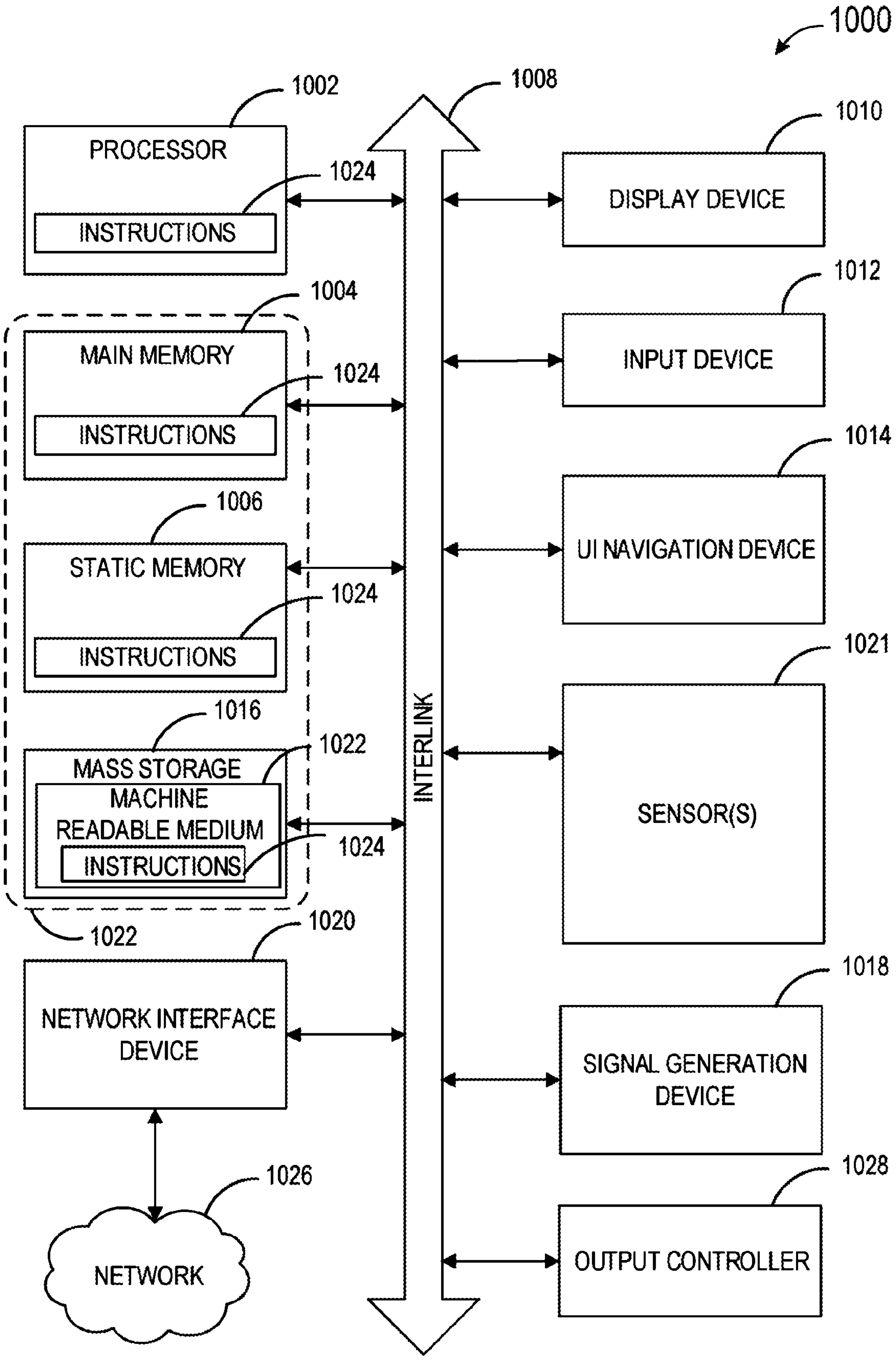
FIG. 18 is a block diagram illustrating an example machine upon which any one or more of the techniques (e.g., methodologies) discussed herein may perform.

FIG. 18 illustrates generally a block diagram of an example machine 1000 upon which any one or more of the techniques (e.g., methodologies) discussed herein may perform. Portions of this description may apply to the computing framework of various portions of the image-guided navigation system 500, such as the image processing unit 510 and the navigation planning unit 520.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010 (e.g., a raster display, vector display, holographic display, etc.), an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensors. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine-readable medium 1022 is illustrated as a single medium, the term "machine readable medium" may include a single medium or multiple media (e.g., a centralized or distributed database, and/or associated caches and servers) configured to store the one or more instructions 1024.

The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1024 may further be transmitted or received over a communication network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communication network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

(1st aspect) An endoscopy planning system, comprising:

a processor configured to:

receive preoperative images of at least a portion of a surgically altered anatomy;

generate an endoscopy plan using the received preoperative images, including determine a navigation route through the surgically altered anatomy toward a target portion in the preoperative images; and output the endoscopy plan to a user or a robotic endoscopy system to perform an endoscopy procedure in accordance with the endoscopy plan.

(2nd aspect) The endoscopy planning system of 1st aspect, wherein the processor is configured to select an endoscope or to determine the navigation route by applying at least one trained machine-learning model to the received preoperative images.

(3rd aspect) The endoscopy planning system of any of 1st to 2nd aspect, wherein the preoperative images include one or more of:

a fluoroscopic image;

a computer-tomography (CT) scan image;

a magnetic resonance imaging (MRI) scan image;

an electrical potential map or an electrical impedance map;

a magnetic resonance cholangiopancreatography (MRCP) image; or an endoscopic ultrasonography (EUS) image.

(4th aspect) The endoscopy planning system of any of 1st to 3rd aspect, wherein the preoperative images include one or more endoscopic images from prior endoscopic procedures.

(5th aspect) The endoscopy planning system of any of 1st to 4th aspect, wherein the processor is configured to:

recognize an anatomical structure and determine one or more positional or geometric parameters of the recognized anatomical structure from the received preoperative images; and generate the endoscopy plan further using the one or more positional or geometric parameters of the recognized anatomical structure.

(6th aspect) The endoscopy planning system of 5th aspect, wherein the processor is configured to apply at least one trained machine-learning model to the received preoperative images to recognize the anatomical structure or determine the one or more positional or geometric parameters.

(7th aspect) The endoscopy planning system of any of 1st to 6th aspect, wherein to generate the endoscopy plan further includes to select an endoscope with a recommended type, size, or length.

(8th aspect) The endoscopy planning system of 7th aspect, wherein the surgically altered anatomy includes an altered gastrointestinal (GI) tract, and wherein the endoscopy plan is with regard to passing the selected endoscope through the altered GI tract into an pancreaticobiliary anatomy.

(9th aspect) The endoscopy planning system of 8th aspect, comprising a user interface configured to receive a user input designating, on at least one of the preoperative images, a starting point and an end point on the altered GI tract for passing the selected endoscope, wherein the processor is configured to select the endoscope and to determine the navigation route further based on the starting point and the end point of the altered GI tract.

(10th aspect) The endoscopy planning system of 8th aspect, wherein the processor is configured to:

determine one or more positional or geometric parameters of the altered GI tract from the received preoperative images of the altered GI tract; and generate the endoscopy plan including selecting the endoscope based at least on the determined one or more positional or geometric parameters of the altered GI tract.

(11th aspect) The endoscopy planning system of 10th aspect, wherein the one or more positional or geometric parameters of the altered GI tract includes an estimated length of the navigation route for passing the selected endoscope in the altered GI tract, wherein the processor is configured to determine the selected endoscope of a particular length based on the estimated length of the navigation route.

(12th aspect) The endoscopy planning system of 10th aspect, wherein the one or more positional or geometric parameters of the altered GI tract includes an estimated angle between the navigation route and a target duct of the pancreaticobiliary anatomy into which the selected endoscope is to reach, wherein the processor is configured to determine the selected endoscope between a forward-viewing endoscope and a side-viewing endoscope based on the estimated angle between the navigation route and the target duct.

(13th aspect) The endoscopy planning system of any of 1st to 12th aspect, wherein the endoscopy plan includes recommended values of one or more operational parameters for operating an endoscope or for manipulating a surgical tool associated therewith during the endoscopy procedure.

(14th aspect) The endoscopy planning system of 13th aspect, wherein the one or more operational parameters include a position, a posture, a heading direction, or an angle for the endoscope or the surgical tool.

(15th aspect) The endoscopy planning system of any of 1st to 14th aspect, wherein the processor is configured to receive preoperative images of a non-surgically altered anatomy, wherein to generate the endoscopy plan includes to determine the navigation route along at least a portion of a gastrointestinal tract toward a target portion in the preoperative images of the non-surgically altered anatomy.

(16th aspect) A method of planning an endoscopy procedure in a surgically altered anatomy, the method comprising:

receiving preoperative images of at least a portion of the surgically altered anatomy;

generating an endoscopy plan using the received preoperative images, including determining a navigation route through the surgically altered anatomy toward a target portion in the preoperative images; and providing the endoscopy plan to a user or a robotic endoscopy system for use in the endoscopy procedure in accordance with the endoscopy plan.

(17th aspect) The method of 16th aspect, wherein generating the endoscopy plan includes applying the received preoperative images to at least one trained machine-learning model to determine the navigation route.

(18th aspect) The method of any of 16th to 17th aspect, comprising:

recognizing an anatomical structure and determining one or more positional or geometric parameters of the recognized anatomical structure from the received preoperative images; and generating the endoscopy plan further using the one or more positional or geometric parameters of the recognized anatomical structure.

(19th aspect) The method of 18th aspect, comprising applying at least one trained machine-learning model to the received preoperative images to recognize the anatomical structure or to determine the one or more positional or geometric parameters.

(20th aspect) The method of any of 16th to 19th aspect, wherein generating the endoscopy plan includes selecting an endoscope with a recommended type, size, or length.

(21th aspect) The method of 20th aspect, wherein the surgically altered anatomy includes an altered gastrointestinal (GI) tract, and wherein the endoscopy plan is with regard to passing the selected endoscope through the altered GI tract into an pancreaticobiliary anatomy.

(22th aspect) The method of 21th aspect, comprising receiving a user input designating, on at least one of the preoperative images, a starting point and an end point on the altered GI tract for passing the selected endoscope, wherein generating the endoscopy plan includes selecting the endoscope and determining the navigation route further based on the starting point and the end point of the altered GI tract.

(23th aspect) The method of 21th aspect, comprising determining one or more positional or geometric parameters of the altered GI tract from the received preoperative images of the altered GI tract, wherein generating the endoscopy plan includes selecting the endoscope based at least on the determined one or more positional or geometric parameters of the altered GI tract.

(24th aspect) The method of 23th aspect, wherein the one or more positional or geometric parameters of the altered GI tract includes an estimated length of the navigation route for passing the selected endoscope in the altered GI tract, wherein generating the endoscopy plan includes determining an endoscope length based on the estimated length of the navigation route.

(25th aspect) The method of 23th aspect, wherein the one or more positional or geometric parameters of the altered GI tract includes an estimated angle between the navigation route and a target duct of the pancreaticobiliary anatomy into which the selected endoscope is to reach, wherein generating the endoscopy plan includes selecting between a forward-viewing endoscope and a side-viewing endoscope based on the estimated angle between the navigation route and the target duct.

(26th aspect) The method of any of 16th to 26th aspect, further comprising receiving preoperative images of a non-surgically altered anatomy, wherein generating the endoscopy plan includes determining the navigation route along at least a portion of a gastrointestinal tract toward a target portion in the preoperative images of the non-surgically altered anatomy.

Systems, devices, and methods for image-based endoscopic procedure planning in patients with altered anatomy such as surgically altered upper gastrointestinal (GI) tract are disclosed. An endoscopy planning system comprises a processor that can receive a plurality of preoperative images of an altered anatomy of a patient, analyze the preoperative images to generate an endoscopy plan including a navigation route through the altered anatomy toward a target portion in the preoperative images. The endoscopy plan can additionally include an endoscope of a selected type and length. The endoscopy plan can be presented to a user on a user interface, or provided to a robotic endoscopy system to facilitate robot-assisted procedure.

What is claimed is:

1. A method for endoluminal transgastric access to a pancreaticobiliary anatomy of a patient, the method comprising:

creating a reversible alteration of gastric anatomy in the patient, including reversibly disconnecting a first gastric portion from a second gastric portion using an alterable gastric closure and a closing device; and during a pancreaticobiliary endoscopy procedure:

passing a steerable elongate instrument through a portion of gastrointestinal (GI) tract into the first gastric portion;

identifying the alterable gastric closure that reversibly disconnects the first and second gastric portions;

disengaging at least a portion of the alterable gastric closure using an endoluminal disengaging device operably disposed at a distal portion of the steerable elongate instrument, the disengagement at least partially reconnecting the first and second gastric portions; and extending the steerable elongate instrument through the disengaged portion of the alterable gastric closure into the second gastric portion and further into the pancreaticobiliary anatomy to perform diagnostic or therapeutic operation therein.

2. The method of claim 1, further comprising, at a conclusion of the pancreaticobiliary endoscopy procedure, reapplying an alterable gastric closure to reversibly disconnect the first gastric portion from the second gastric portion using the closing device.

3. The method of claim 1, wherein the diagnostic or therapeutic operation includes an endoscopic cholangiopancreatography (ERCP) procedure or a direct peroral cholangioscopy (DPOC) procedure.

4. The method of claim 1, wherein the first and second gastric portions are respectively a gastric pouch and an excluded stomach portion identified in a gastric bypass procedure.

5. The method of claim 1, wherein reversibly disconnecting the first gastric portion from the second gastric portion includes using an endoluminal closing device operably disposed at a distal portion of the steerable elongate instrument.

6. The method of claim 1, wherein the alterable gastric closure includes at least one of:

alterable sutures;

alterable glue; or alterable clips.

7. The method of claim 1, comprising:

identifying position and posture of one or more of the closing device or the endoluminal disengaging device; and providing the identified position and posture of one or more of the closing device or the endoluminal disengaging device to a user on a user interface, or to a robotic endoscopy system to facilitate robotic manipulation of the closing device or the endoluminal disengaging device.

8. The method of claim 7, comprising receiving endoscopic image of the portion of the GI tract, wherein identifying the position and posture of one or more of the closing device or the endoluminal disengaging device is based at least on the received endoscopic image.

9. The method of claim 8, comprising:

receiving from the user interface a user input identifying closing site and trajectory on the endoscopic image of the portion of the GI tract; and robotically manipulating the closing device to apply the alterable gastric closure to the identified closing site and trajectory.

10. The method of claim 8, comprising, when creating the reversible alteration of gastric anatomy:

identifying position and posture of a laparoscopic device used in a gastric bypass procedure from the endoscopic image; and presenting the endoscopic image of the portion of the GI tract and the identified position and posture of the laparoscopic device to a user on a user interface.

11. The method of claim 7, comprising detecting electromagnetic (EM) wave emitted from an EM emitter associated with one or more of the closing device or the endoluminal disengaging device, wherein identifying the position and posture of one or more of the closing device or the endoluminal disengaging device is based at least on the detected EM waves.

12. The method of claim 7, comprising:

receiving an endoscopic image of the portion of the GI tract during the pancreaticobiliary endoscopy procedure;

identifying disengaging site and trajectory in proximity to the alterable gastric closure from the received endoscopic image; and robotically manipulating the endoluminal disengaging device to disengage at least the portion of the alterable gastric closure from the identified disengaging site and trajectory.

13. The method of claim 12, comprising receiving a user input identifying the disengagement site and trajectory from the endoscopic image.

14. The method of claim 12, wherein identifying the disengaging site and trajectory includes detecting a marker on at least a portion of the alterable gastric closure being applied when creating the reversible alteration of gastric anatomy.

15. The method of claim 1, comprising presenting on a user interface an interactive and navigable view of an image of the reversibly altered gastric anatomy with distinct landmarks.

* * * * *